United States Patent
Hybertson et al.

(10) Patent No.: US 11,413,269 B2
(45) Date of Patent: Aug. 16, 2022

(54) COMPOSITIONS FOR IMPROVED NRF2 ACTIVATION AND METHODS OF THEIR USE

(71) Applicant: PATHWAYS BIOSCIENCE, LLC, Aurora, CO (US)

(72) Inventors: Brooks Michael Hybertson, Boulder, CO (US); Joe Milton McCord, West Palm Beach, FL (US)

(73) Assignee: PATHWAYS BIOSCIENCE, LLC, Aurora, CO (US)

(*) Notice: Subject to any disclaimer, the term of this patent is extended or adjusted under 35 U.S.C. 154(b) by 0 days.

(21) Appl. No.: 15/757,270

(22) PCT Filed: Sep. 2, 2016

(86) PCT No.: PCT/US2016/050292
§ 371 (c)(1),
(2) Date: Mar. 2, 2018

(87) PCT Pub. No.: WO2017/041054
PCT Pub. Date: Mar. 9, 2017

(65) Prior Publication Data
US 2018/0250264 A1 Sep. 6, 2018

Related U.S. Application Data

(60) Provisional application No. 62/355,810, filed on Jun. 28, 2016, provisional application No. 62/214,175, filed on Sep. 3, 2015.

(51) Int. Cl.
| | |
|---|---|
| *A61K 36/53* | (2006.01) |
| *A61K 36/81* | (2006.01) |
| *A61K 36/906* | (2006.01) |
| *A61K 36/00* | (2006.01) |
| *A61K 31/366* | (2006.01) |
| *A61K 31/12* | (2006.01) |
| *A61K 31/352* | (2006.01) |
| *A61K 36/9068* | (2006.01) |
| *A61K 36/28* | (2006.01) |
| *A61K 36/68* | (2006.01) |
| *A61K 31/365* | (2006.01) |
| *A61P 39/06* | (2006.01) |
| *A61P 29/00* | (2006.01) |
| *A61K 31/192* | (2006.01) |
| *A61K 31/585* | (2006.01) |

(52) U.S. Cl.
CPC ........ *A61K 31/366* (2013.01); *A61K 31/12* (2013.01); *A61K 31/192* (2013.01); *A61K 31/352* (2013.01); *A61K 31/365* (2013.01); *A61K 31/585* (2013.01); *A61K 36/28* (2013.01); *A61K 36/53* (2013.01); *A61K 36/68* (2013.01); *A61K 36/81* (2013.01); *A61K 36/9068* (2013.01); *A61P 29/00* (2018.01); *A61P 39/06* (2018.01)

(58) Field of Classification Search
None
See application file for complete search history.

(56) References Cited

U.S. PATENT DOCUMENTS

| | | | |
|---|---|---|---|
| 5,888,514 A * | 3/1999 | Weisman | A61K 35/32 424/523 |
| 9,381,221 B2 * | 7/2016 | Velez-Rivera | A61K 36/28 |
| 2009/0274746 A1 | 11/2009 | Gupta et al. | |
| 2009/0304823 A1 * | 12/2009 | Offord Cavin | A61K 36/53 424/725 |
| 2011/0177182 A1 | 7/2011 | Ianiro et al. | |
| 2013/0023489 A1 | 1/2013 | Kubow et al. | |
| 2014/0193480 A1 | 7/2014 | McWherter et al. | |
| 2014/0271944 A1 | 9/2014 | McCord et al. | |
| 2014/0287071 A1 | 9/2014 | Barnett, III | |

FOREIGN PATENT DOCUMENTS

| | | | |
|---|---|---|---|
| IN | 200701648 I4 * | 10/2009 | |
| JP | 2011057654 A | 3/2011 | |
| JP | 2013209351 A | 10/2013 | |
| KR | 2011130125 A * | 12/2011 | |
| WO | WO 2014/151891 A1 | 9/2014 | |
| WO | WO2015008301 A1 * | 1/2015 | |
| WO | WO 2016/037971 A1 | 3/2016 | |

OTHER PUBLICATIONS

Aggarwal et al. (2004) "From chemoprevention to chemotherapy: common targets and common goals." Expert Opin Investig Drugs, 13(10), pp. 1327-1338.
Anadon et al. (2008) "Acute oral safety study of rosemary extracts in rats." J Food Prot, 71(4), pp. 790-795.
Baitharu et al. (2014) "Withanolide A prevents neurodegeneration by modulating hippocampal glutathione biosynthesis during hypoxia." PLoS One 9(10): e105311.
Bjelakovic et al. (2007) "Mortality in randomized trials of antioxidant supplements for primary and secondary prevention: systematic review and meta-analysis." JAMA, 297(8), pp. 842-857.
Bocci et al. (2015) "Nrf2 activation as target to implement therapeutic treatments." Front Chem, 3, p. 4.
Boon et al. (2004) "Botanical medicine and cancer: a review of the safety and efficacy." Expert Opin Pharmacother, 5(12), pp. 2485-2501.
Boutten et al. (2010) "Oxidative stress targets in pulmonary emphysema: focus on the Nrf2 pathway." Expert Opin Ther Targets, 14(3), pp. 329-346.
Bozin et al. (2007) "Antimicrobial and antioxidant properties of rosemary and sage (*Rosmarinus officinalis* L. and *Salvia officinalis* L., *Lamiaceae*) essential oils." J Agric Food Chem, 55(19), pp. 7879-7885.

(Continued)

*Primary Examiner* — Michael Barker
*Assistant Examiner* — Randall O Winston
(74) *Attorney, Agent, or Firm* — Lathrop GPM LLP

(57) ABSTRACT

Disclosed here are compositions and methods for preventing or treating certain health conditions associated with inflammation or oxidative stress. These compositions are prepared from ingredients containing phytochemicals that activate the Nrf2 pathways. Synergistic effects of the different phytochemicals are also disclosed.

14 Claims, 12 Drawing Sheets

(56) References Cited

OTHER PUBLICATIONS

Chandrasekhar et al. (2012) "A prospective, randomized double-blind, placebo-controlled study of safety and efficacy of a high-concentration full-spectrum extract of ashwagandha root in reducing stress and anxiety in adults." Indian J Psychol Med, 34(3), pp. 255-262.
Cho et al. (2010). "Nrf2 protects against airway disorders." Toxicol Appl Pharmacol, 244(1), pp. 43-56.
Chun et al. (2007) "Estimated dietary flavonoid intake and major food sources of U.S. adults." J Nutr, 137(5), pp. 1244-1252.
Chun et al. (2014) "Carnosol: A Phenolic Diterpene With Cancer Chemopreventive Potential." J Cane Prev, 19, pp. 103-110.
Del Campo et al. (2000) "Antimicrobial effect of rosemary extracts." J Food Prot, 63(10), pp. 1359-1368.
Eggler et al. (2008) "Molecular mechanisms of natural products in chemoprevention: induction of cytoprotective enzymes by Nrf2." Mol Nutr Food Res, 52 Suppl 1, pp. S84-S94.
Emami et al. (2013) "Hydroalcoholic extract of Rosemary (*Rosmarinus officinalis* L.) and its constituent carnosol inhibit formalin-induced pain and inflammation in mice." Pak J Biol Sci, 16 (7), pp. 309-316.
Gonzalez-Vallinas et al. (2015) "Rosemary (*Rosmarinus officinalis* L.) Extract as a Potential Complementary Agent in Anticancer Therapy." Nutr Cancer, pp. 1-9.
Heistad et al. (2009) "Novel aspects of oxidative stress in cardiovascular diseases." Circ J, 73(2), pp. 201-207.
Huang et al. (2015) "The complexity of the Nrf2 pathway: Beyond the antioxidant response." The Journal of Nutritional Biochemistry, 26, pp. 1401-1413.
Hybertson et al. (2014) "Role of the Nrf2 signaling system in health and disease." Clin Genet, 86(5), pp. 447-452.
Jacobs et al. (2002) "Milk thistle for the treatment of liver disease: a systematic review and meta-analysis." Am J Med, 113(6), pp. 506-515.
Johnson et al. (2015) "Nrf2-a therapeutic target for the treatment of neurodegenerative diseases." Free Radic Biol Med., 88, pp. 253-267.
Johnson (2011) "Carnosol: A promising anti-cancer and anti-inflammatory agent." Cancer letters 305(1), pp. 1-7.
Jun et al. (2015) "Estimation of dietary flavonoid intake and major food sources of Korean adults." Br J Nutr, pp. 1-10.
Kaufman et al. (2015) "Fyn inhibition rescues established memory and synapse loss in Alzheimer mice." Ann Neurol, 77(6), pp. 953-971.
Wakabayashi et al. (2010) "When Nrf2 Talks, Who's Listening?" Antioxid Redox Signal., vol. 13, No. 11, 16 pp.
Khan et al. (2015) "Effect of Withania somnifera (Ashwagandha) root extract on amelioration of oxidative stress and autoantibodies production in collagen-induced arthritic rats." J Complement Integr Med, 12(2), pp. 117-125.
Kim et al. (2015) "Intake and major sources of dietary flavonoid in Korean adults: Korean National Health and Nutrition Examination Survey 2010-2012." Asia Pac J Clin Nutr, 24(3), pp. 456-463.
Klancnik et al. (2009). "In vitro antimicrobial and antioxidant activity of commercial rosemary extract formulations." J Food Prot, 72(8), pp. 1744-1752.
Koehn (2006) "Therapeutic potential of natural product signal transduction agents." Curr Opin Biotechnol, 17(6), pp. 631-637.
Koehn et al. (2005) "The evolving role of natural products in drug discovery." Nat Rev Drug Discov, 4(3), pp. 206-220.
Kumar et al. (2015) "Efficacy & safety evaluation of Ayurvedic treatment (Ashwagandha powder & Sidh Makardhwaj) in rheumatoid arthritis patients: a pilot prospective study." Indian J Med Res, 141(1), pp. 100-106.
Lakhan et al. (2015) "Zingiberaceae extracts for pain: a systematic review and meta-analysis." Nutr J, 14, p. 50.
Lee (2010) "Discovery and development of natural product-derived chemotherapeutic agents based on a medicinal chemistry approach." J Nat Prod, 73(3), pp. 500-516.

Maher (2010) "The rise of antioxidant signaling—the evolution and hormetic actions of Nrf2." Toxicol Appl Pharmacol, 244(1), pp. 4-15.
Martin et al. (2004) "Regulation of Heme Oxygenase-1 Expression through the Phosphatidylinositol 3-Kinase/Akt Pathway and the Nrf2 Transcription Factor in Response to the Antioxidant Phytochemical Carnosol." Journal of Biological Chemistry, 279(10), pp. 8919-8929.
Mishra et al. (2000) "Scientific basis for the therapeutic use of Withania somnifera (ashwagandha): a review." Altern Med Rev, 5(4), pp. 334-346.
Moon et al. (2015) "Dual roles of NRF2 in tumor prevention and progression: possible implications in cancer treatment." Free Radic Biol Med, 79, pp. 292-299.
Nabavi et al. (2015) "Luteolin as an anti-inflammatory and neuroprotective agent: A brief review." Brain Research Bulletin, 119, Part A: pp. 1-11.
Nilius et al. (2013) "Spices: The Savory and Beneficial Science of Pungency." Rev Physiol Biochem Pharmacol, 76 pp.
Ortuno et al. (2015) "Antioxidant and antimicrobial effects of dietary supplementation with rosemary diterpenes (carnosic acid and carnosol) vs vitamin E on lamb meat packed under protective atmosphere." Meat Sci, 110, pp. 62-69.
Paredes et al. (2015) "Induction of NRF2-mediated gene expression by dietary phytochemical flavones apigenin and luteolin." Biopharm Drug Dispos., 12 pp.
Pechanova et al. (2009) "Chronic antioxidant therapy fails to ameliorate hypertension: potential mechanisms behind." J Hypertens, 27, Suppl 6: S32-36.
Petiwala et al. (2015) "Diterpenes from rosemary (*Rosmarinus officinalis*): Defining their potential for anti-cancer activity." Cancer Lett, 367(2), pp. 93-102.
Priyandoko et al. (2011) "Ashwagandha leaf derived withanone protects normal human cells against the toxicity of methoxyacetic acid, a major industrial metabolite." PLoS One, 6(5): e19552.
Raghavan et al. (2015) "Withania somnifera: a pre-clinical study on neuroregenerative therapy for stroke." Neural Regen Res, 10(2), pp. 183-185.
Rai et al. (2016) "Anticancer activities of Withania somnifera: Current research, formulations, and future perspectives." Pharm Biol, 54(2), pp. 189-197.
Raskovic et al. (2014) "Antioxidant activity of rosemary (*Rosmarinus officinalis* L.) essential oil and its hepatoprotective potential." BMC Complement Altern Med, 14, p. 225.
Roodenrys et al. (2002) "Chronic effects of Brahmi (*Bacopa monnieri*) on human memory." Neuropsychopharmacology, 27(2), pp. 279-281.
Saller et al. (2001) "The use of silymarin in the treatment of liver diseases." Drugs, 61(14), pp. 2035-2063.
Saremi et al. (2009) "Vitamin E and Cardiovascular Disease." Am J Ther., 17(3), 10 pp.
Satoh et al. (2010) "Nrf2-deficiency creates a responsive microenvironment for metastasis to the lung." Carcinogenesis, 31(10), pp. 1833-1843.
Satoh et al. (2008) "Carnosic acid, a catechol-type electrophilic compound, protects neurons both in vitro and in vivo through activation of the Keap1/Nrf2 pathway via S-alkylation of targeted cysteines on Keap1." J Neurochem, 104(4), pp. 1116-1131.
Seelinger et al. (2008). "Anti-oxidant, anti-inflammatory and anti-allergic activities of luteolin." Planta Med, 74(14), pp. 1667-1677.
Sekhar et al. (2015) "NRF2 promotes survival following exposure to ionizing radiation." Free Radic Biol Med., 88(0 0), pp. 268-274.
Shukla et al. (2012) "Profiling environmental chemicals for activity in the antioxidant response element signaling pathway using a high throughput screening approach." Environ Health Perspect, 120(8), pp. 1150-1156.
Simmons et al. (2011) "NRF2 Oxidative Stress Induced by Heavy Metals is Cell Type Dependent." Curr Chem Genomics, 5, pp. 1-12.
Sun et al. (2012) "Oxidative stress suppression by luteolin-induced heme oxygenase-1 expression." Toxicol Appl Pharmacol, 265(2), pp. 229-240.
Suzuki et al. (2015) "Molecular basis of the Keap1-Nrf2 system." Free Radic Biol Med., 88, pp. 93-100.

(56) References Cited

OTHER PUBLICATIONS

Taliou et al. (2013) "An open-label pilot study of a formulation containing the anti-inflammatory flavonoid luteolin and its effects on behavior in children with autism spectrum disorders." Clin Ther, 35(5), pp. 592-602.
Theoharides et al. (2012) "A case series of a luteolin formulation (NeuroProtek(R)) in children with autism spectrum disorders." Int J Immunopathol Pharmacol, 25(2), pp. 317-323.
Vaishnavi et al. (2012) "Differential activities of the two closely related withanolides, Withaferin A and Withanone: bioinformatics and experimental evidences." PLoS One 7(9): e44419.
Velmurugan et al. (2009) "Synergistic induction of heme oxygenase-1 by the components of the antioxidant supplement Protandim." Free Radic Biol Med, 46(3), pp. 430-440.
Wang et al. (2014) "Biological properties of 6-gingerol: a brief review." Nat Prod Commun, 9(7), pp. 1027-1030.
Wankhede et al. (2015) "Examining the effect of Withania somnifera supplementation on muscle strength and recovery: a randomized controlled trial." J Int Soc Sports Nutr, 12, p. 43.
Wen et al. (2011) "Discovery of molecular mechanisms of traditional Chinese medicinal formula Si-Wu-Tang using gene expression microarray and connectivity map." PLoS One 6(3): e18278.
Wilson (2015). "Ginger (*Zingiber officinale*) as an Analgesic and Ergogenic Aid in Sport: A Systemic Review." J Strength Cond Res, 29(10), pp. 2980-2995.
Wu et al. (2015) "Luteolin and Apigenin Attenuate 4-Hydroxy-2-Nonenal-Mediated Cell Death through Modulation of UPR, Nrf2-ARE and MAPK Pathways in PC12 Cells." PLoS One, 10(6), e0130599.
Xiang et al. (2013) "Carnosic acid attenuates lipopolysaccharide-induced liver injury in rats via fortifying cellular antioxidant defense system." Food and Chemical Toxicology, 53(0), pp. 1-9.
Xu et al. (2014). "Luteolin provides neuroprotection in models of traumatic brain injury via the Nrf2-ARE pathway." Free Radic Biol Med, 71, pp. 186-195.
Zhang et al. (2013) "Antioxidant and Nrf2 inducing activities of luteolin, a flavonoid constituent in lxeris sonchifolia Hance, provide neuroprotective effects against ischemia-induced cellular injury." Food Chem Toxicol, 59, pp. 272-280.
Zick et al. (2008). "Pharmacokinetics of 6-gingerol, 8-gingerol, 10-gingerol, and 6-shogaol and conjugate metabolites in healthy human subjects." Cancer Epidemiol Biomarkers Prev, 17(8), pp. 1930-1936.
PCT/US16/50292 International Search Report and Written Opinion dated Dec. 2, 2016, 13 pages.
Chilean patent application No. 578-2018, English summary of Office Action, dated Nov. 13, 2019, 6 pages.
Chinese Patent Application No. 201680050647.0, Office Action dated Mar. 27, 2020, with English translation, 13 pages.
Colombian Patent Application No. NC2018/0003454, English translation of Office Action, dated Jan. 22, 2020 dated Mar. 3, 2020, 8 pages.
Japanese Patent Application No. 2018-531303, Office Action dated Jul. 15, 2020, with English translation, 6 pages.
Chen, H. et al., "Ginger Compound [6]-Shogaol and Its Cysteine-Conjugated Metabolite (M2) Activate Nrf2 in Colon Epithelial Cells in Vitro and in Vivo" Chem Res Toxicol. Sep. 15, 2014; 27(9): 1575-1585.
Dinkova-Kostova, A. "The Role of Sulfhydryl Reactivity of Small Molecules for the Activation of the KEAP1/NRF2 Pathway and the Heat Shock Response", Hindawi Publishing Corporation, Scientifica vol. 2012, Article ID 606104, 19 pages.
Satoh, T. et al. "Nrf2/ARE-Mediated Antioxidant Actions of Pro-Electrophilic Drugs" Free Radical Biology and Medicine, vol. 65, Dec. 2013, pp. 645-657.
Bak, M.-J., et al. "6-shogaol-rich extract from ginger up-regulates the antioxidant defense systems in cells and mice" Molecules, Jul. 4, 2012;17(7): pp. 8037-8055.
Japanese Patent Application No. 2018-531303, Office Action dated Feb. 5, 2021, with English translation, 4 pages.
Chinese Patent Application No. 201680050947.0, Second Office Action dated Jan. 26, 2021, with brief summary in English, 6 pages.
Japanese Patent Application No. 2018-531303, Decision to Grant a Patent dated May 24, 2021, with English translation, 5 pages.
Colombian Patent Application No. NC2018/0003454, Second Office Action dated Mar. 15, 2021, with English translation, 23 pages.
Chinese Patent Application No. 201680050947.0, Office Action dated Aug. 23, 2021, with English translation, 19 pages.
Peruvian Patent Application No. 000340-2018/DIN, Office Action dated Sep. 30, 2021, with English translation, 13 pages.
Mexican Patent Application No. MX/a/2018/002743, Office Action dated Jan. 17, 2022, with English translation, 7 pages.
Chinese Patent Application No. 201680050947.0, Decision of Rejection dated Jan. 19, 2022, with English summary, 6 pages.

\* cited by examiner

COMPOSITIONS FOR IMPROVED NRF2 ACTIVATION AND METHODS OF THEIR USE

RELATED APPLICATIONS

This application claims priority to U.S. Patent application 62/214,175 filed Sep. 3, 2015, and U.S. Patent application 62/355,810 filed Jun. 28, 2016, the entire content of which is hereby incorporated by reference into this application.

BACKGROUND

I. Field of the Invention

The present disclosure relates to methods and compositions for preventing or treating certain health conditions. More particularly, the present disclosure relates to compositions and methods for preventing or treating certain health conditions associated with inflammation and/or oxidative stress.

II. Description of the Related Art

Nuclear factor-erythroid 2 related factor 2 (Nrf2) is a transcription factor that is regulated by Kelch-like ECH-Associated Protein 1 (Keap1). Nrf2 regulates gene expression of a wide variety of cytoprotective phase II detoxification enzymes and antioxidant enzymes through an enhancer sequence known as the antioxidant-responsive element (ARE) (Maher and Yamamoto 2010, Satoh, Moriguchi et al. 2010). Relevant to oxidative stress, the ARE is a promoter element found in many antioxidant enzymes, including superoxide dismutase (SOD), peroxiredoxins, thioredoxins, catalase, glutathione peroxidase, and heme oxygenase-1 (HO-1). Nrf2 plays a pivotal role in the ARE-driven cellular defense system against oxidative stress. See, Kensler, Wakabayashi et al. 2010; Hybertson and Gao 2014, Bocci and Valacchi 2015, Huang, Li et al. 2015, Johnson and Johnson 2015, Moon and Giaccia 2015, Petiwala and Johnson 2015, Sekhar and Freeman 2015, Suzuki and Yamamoto 2015.

SUMMARY

The presently disclosed instrumentalities advance the art by providing combinations of agents that activate the Nrf2 cell signaling pathway. In one embodiment, the combinations of agents may activate the Nrf2 pathway more effectively than individual agents. In another embodiment, the combinations of agents may activate the Nrf2 pathway synergistically.

In one embodiment, combinations of more than one ingredients are disclosed here. In one aspect, each ingredient may contain one or more phytochemicals. In another aspect, these phytochemicals may be found in rosemary (*Rosmarinus officinalis*), ginger (*Zingiber officinale*), luteolin (from *Sophora Japonica*), milk thistle (*Silybum marianum*), and *Bacopa* (*Bacopa monnieri*). In another aspect, the phytochemicals components are carnosol, shogaol, luteolin, silymarin, and bacosides, which may be found in rosemary, ginger, luteolin, milk thistle, and *Bacopa*, respectively. In another aspect, the disclosed compositions induce ARE-regulated antioxidant genes by the Nrf2-dependent pathway.

In another embodiment, specific combinations of rosemary, ashwagandha, and luteolin (referred to herein as PB125), specific combinations of rosemary, ginger, luteolin, and silymarin (referred to herein as PB127), and specific combinations of rosemary, ginger, luteolin, silymarin, and *Bacopa* (referred to herein as PB129) are disclosed. In another embodiment, the combination of these agents may result in a synergistic Nrf2 activation, greater than simply the sum of their individual Nrf2 activation contributions. The active agents or combinations of the agents may be candidates for possible drug development. See, e.g., Koehn and Carter 2005, Lee 2010.

In another embodiment, the disclosed compositions may contain rosemary (carnosol), ginger (6-shogaol and 6-gingerol), ashwagandha (withaferin A), milk thistle (silymarin), *Bacopa monnieri* (bacosides) and luteolin.

In one aspect, the compositions may be administered orally, for example in the form of a tablet, capsule, softgel, syrup, aqueous solution or suspension, alcohol-extract, or powder. In another aspect, the synergistic compositions may be administered in the form of aerosol, for example to the lungs in the form of a fine aerosol mist or powder which is inhaled and partially deposited within the lung airways. In another aspect, the disclosed compositions may be administered by local administration, for example, by applying to the skin in the form of a lotion, gel, ointment, aqueous spray, or within a bandage applied to the skin or to a wound.

In another embodiment, the disclosed composition may contain a combination of rosemary extract (specified at 5 to 10% carnosol), ginger extract (specified at 1-10% 6-shogaol and/or 10-25% 6-gingerol), and luteolin (specified at 95-98% luteolin), in the mass ratio of 10:5:1, respectively. This formula is also referred to as PB123 in this disclosure.

In another embodiment, the disclosed composition may contain a combination of rosemary extract (specified at 5 to 10% carnosol), ashwagandha extract (specified at 1-3% withaferin A), and luteolin (specified at 95-98% luteolin), in the mass ratio of 30:10:4, respectively. This formula is also referred to as PB125 in this disclosure.

In another embodiment, the disclosed composition may contain a combination of rosemary extract (specified at 5 to 10% carnosol), ginger extract (specified at 1-10% 6-shogaol and/or 10-25% 6-gingerol), luteolin (specified at 90-100% luteolin), and milk thistle extract (specified at 50-90% silymarin), in the mass ratio of 10:5:1:30, respectively. This formula is also referred to as PB127 in this disclosure.

In another embodiment, the disclosed composition may contain a combination of rosemary extract (specified at 5 to 10% carnosol), ginger extract (specified at 1-10% 6-shogaol and/or 10-25% 6-gingerol), luteolin (specified at 90-100% luteolin), milk thistle extract (specified at 50-90% silymarin), and *Bacopa monnieri* extract (specified at 10-60% bacosides) in the mass ratio of 10:5:1:30:48, respectively. This formula is also referred to as PB129 in this disclosure.

In another embodiment, the disclosed composition may contain a combination of rosemary extract (specified at 5 to 10% carnosol), ginger extract (specified at 1-10% 6-shogaol and/or 10-25% 6-gingerol), luteolin (specified at 90-100% luteolin), and *Bacopa monnieri* extract (specified at 10-60% bacosides) in the mass ratio of 10:5:1:48, respectively. This formula is also referred to as PB131 in this disclosure.

In another embodiment, PB123 may be administered at 10 to 1000 mg per day as an oral administration to a human. For example, it may be administered as a pill, softgel, or capsule to induce Nrf2 activation, and/or to reduce inflammation and oxidative stress, and/or to improve overall health and wellness.

In another embodiment, PB123 may be administered at 10 to 1000 mg per day as an oral administration to a human to improve protein homeostasis, and/or to prevent aging-related problems associated with protein homeostasis and/or autophagy in humans.

In another embodiment, PB125 or PB127 or PB129 or PB131 may be administered at 10 to 1000 mg per day as an oral administration to a human. For example, it may be administered as a pill, softgel, or capsule to induce Nrf2 activation, and/or to reduce inflammation and oxidative stress, and/or to improve overall health and wellness.

In another embodiment, PB125 or PB127 or PB129 or PB131 may be administered at 10 to 1000 mg per day as an oral administration to a human to improve protein homeostasis, and/or to prevent aging-related problems associated with protein homeostasis and/or autophagy in humans.

DETAILED DESCRIPTION

The Nrf2/ARE pathway has been implicated in the control of oxidative stress (Eggler, Gay et al. 2008, Cho and Kleeberger 2010, Huang, Li et al. 2015, Johnson and Johnson 2015). Certain agents and combinations of such agents (e.g., PB125) that target the Nrf2/ARE pathway may have beneficial effects on cellular function and survival. In one embodiment, these agents and combinations thereof may alleviate inflammatory responses and oxidative stress, and may have beneficial effects on health and wellness.

Prior studies have failed to demonstrate the therapeutic potential of direct antioxidant vitamins or supplements such as vitamins C and E, carotenoids, N-acetylcysteine, and other compounds that react stoichiometrically with reactive oxygen species (ROS) such as superoxide and hydrogen peroxide. Here, an improved antioxidant defenses is demonstrated by using Nrf2 activating combinations (Koehn 2006, Eggler, Gay et al. 2008, Boutten, Goven et al. 2010, Cho and Kleeberger 2010).

Figure 1:
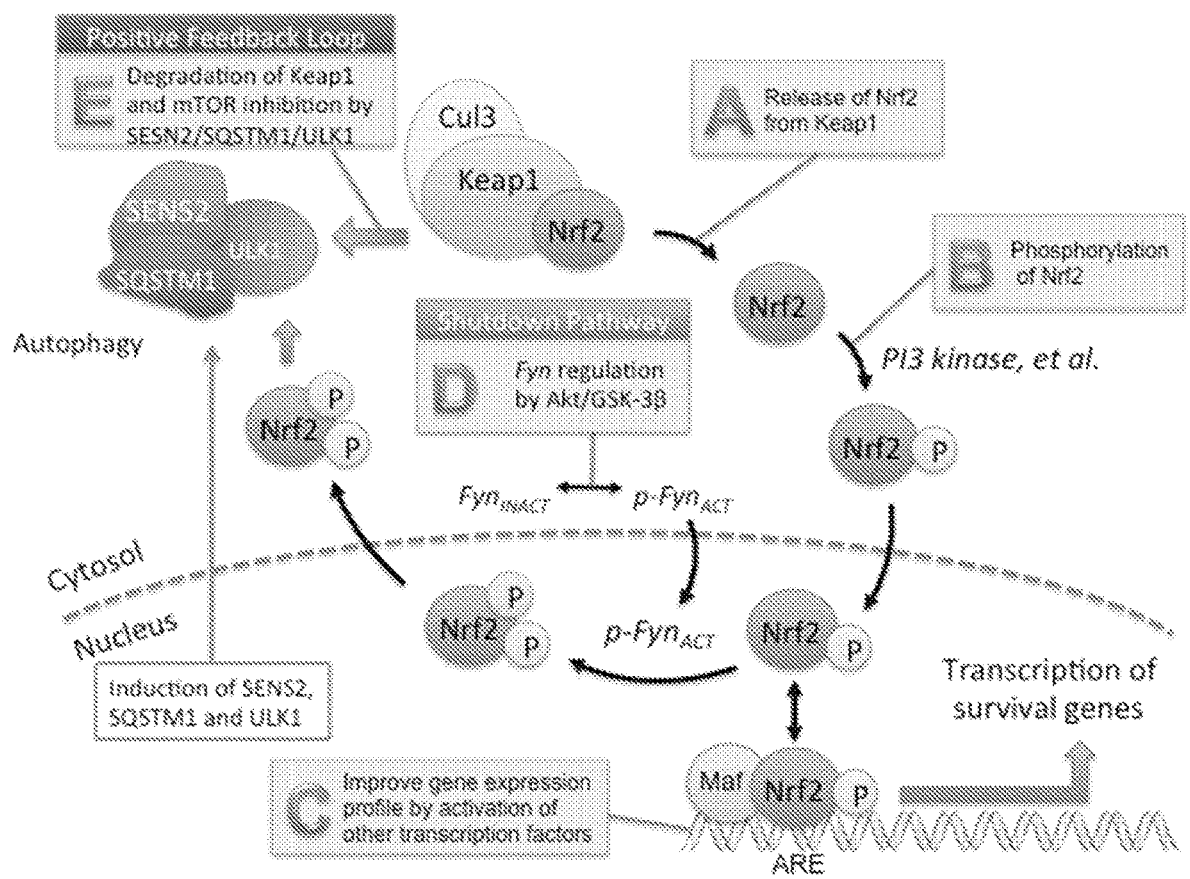
FIG. 1 shows the Nrf2 activation pathways and control points.
Figure 2:
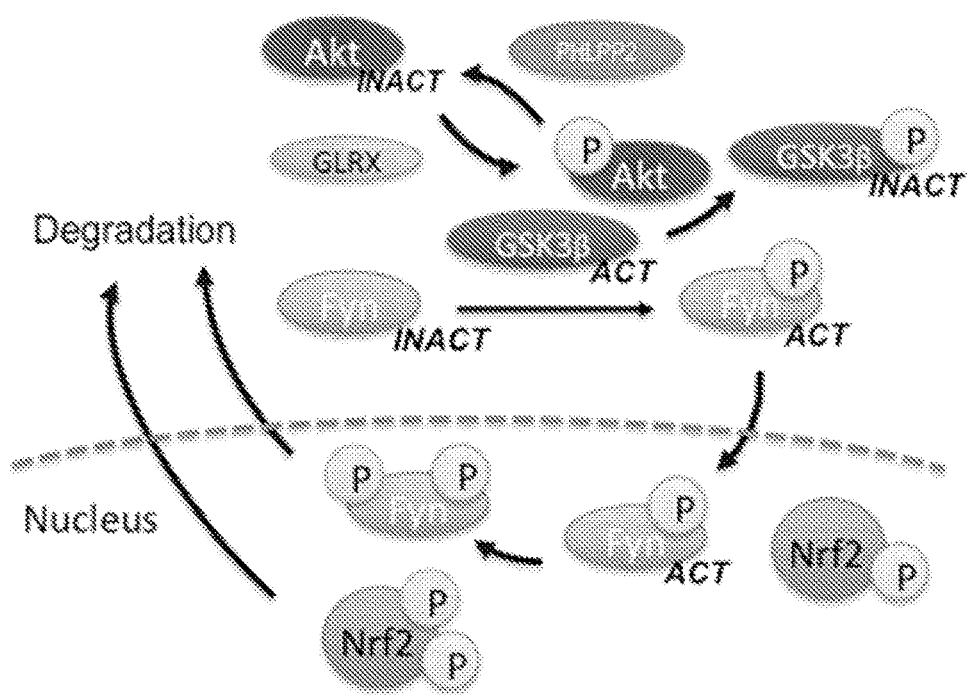
FIG. 2 shows the "Shutdown Pathway"-Fyn-dependent deactivation of nuclear Nrf2.
Figure 3:
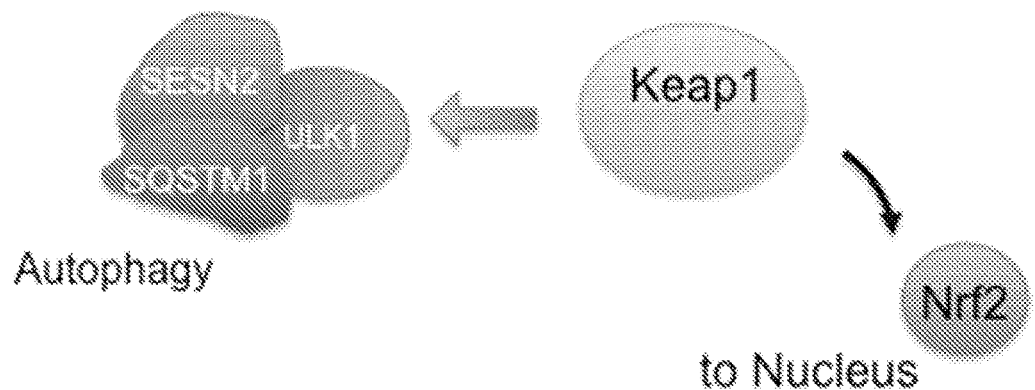
FIG. 3 shows the "Positive Feedback Loop"-Keap1 degradation by Nrf2-induced gene products.

In the present disclosure, a multiplicity of agents were combined in a novel way, i.e., by acting at different control points in the Nrf2 activation pathway. FIG. 1 shows Nrf2 activation pathways and control points A, B, C, D, and E at which low concentrations of agents that act at those control points work together to effect desired Nrf2-dependent gene expression by combinations such as PB125, PB127, and PB129. In the basal state Nrf2 is sequestered and kept inactive by Kelch-like ECH-associated protein 1 (Keap1), which targets Nrf2 for polyubiquitination and degradation by the proteasome. A. Nrf2 activation involves oxidation of specific thiol residues of Keap1, causing it to Nrf2 to be released from Keap1. B. Nrf2 phosphorylation may play a role in targeting it for nuclear import. C. Nrf2 translocation into the nucleus enables Nrf2 to bind promotors containing the Antioxidant Response Element (ARE), initiating transcription of cytoprotective programming D. Inactive cytosolic Fyn may be phosphorylated by GSK3Kβ, and this now active p-Fyn translocates to the nucleus, where it can phosphorylate Nrf2 at a second site resulting in nuclear export and degradation. E. A "positive feedback loop" involves SESN2, SQSTM1 and ULK1, gene products induced by Nrf2. SESN2, SQSTM1 and ULK1 collaborate to activate autophagy of Keap1, liberating more Nrf2, which induces more of these gene products, tending to maintain Nrf2 activation once this positive feedback loop has been triggered.

Also in the present disclosure, the combinations of agents gave surprisingly high Nrf2 activation levels compared to what would be predicted based on the prior art and also based on concurrent experiments examining the Nrf2 activating properties of each agent alone and what would be predicted based on adding them together. The Nrf2 activation by the combination of the agents show a synergistic effect. See, e.g., FIGS. 6 and 7.

An embodiment of the present disclosure comprises combinations of dietary agents—such as in the PB125, PB127, and PB129 combinations—that act on Nrf2 activation by engagement of different, specific control points so that the combination of agents that synergistically activate the Nrf2 pathway. Thus the new combinations of agents that act on different control points of the Nrf2 signaling pathway to increase expression of Nrf2-dependent genes are novel.

By way of example, a number of embodiments of the present disclosure are listed below:

Item 1. A composition comprising two or more phytochemicals selected from the group consisting of carnosol, carnosic acid, shogaol, gingerol, luteolin, and withaferin A, said one or more phytochemicals being present in the composition in an amount effective to activate the Nrf2 (Nuclear factor-erythroid 2 related factor 2) pathway.

Item 2. The composition of Item 1, wherein the two or more phytochemicals exert their effects on at least two different control points of the Nrf2 activation pathway when administered to a mammal, said control points being selected from the group consisting of control points A, B, C, D and E. In one embodiment, at least one of the phytochemicals exerts its effects on one control point, while at least another phytochemical exerts its effects on a different control point of the Nrf2 activation pathway as depicted in FIG. 1.

Item 3. The composition of any of the preceding Items, wherein the two or more phytochemicals have a synergistic effect on Nrf2 activation when administered to a mammal.

Item 4. The composition of any of the preceding Items, wherein the composition comprises at least two ingredients selected from the group consisting of rosemary, ginger, luteolin, and ashwagandha.

Item 5. The composition of any of the preceding Items, wherein the composition also comprises one or more phytochemicals selected from the group consisting of milk thistle and *Bacopa*.

Item 6. The composition of any of the preceding Items, wherein the composition comprises rosemary extract, ginger extract, and luteolin, said rosemary extract being specified at 5-10% carnosol, said ginger extract being specified at 10-20% 6-shogaol, said luteolin being specified at 95-99% luteolin, wherein the ratio between rosemary extract, ginger extract, and luteolin in the composition is approximately 10:5:1 (w/w).

Item 7. The composition of any of the preceding Items, wherein the composition comprises rosemary extract, ashwagandha extract, and luteolin, said rosemary extract being specified at 5-10% carnosol, said ashwagandha extract being specified at 1-3% withaferin A, said luteolin being specified at 95-99% luteolin, wherein the ratio between said rosemary extract, ashwagandha extract, and luteolin in the composition is approximately 30:10:4 (w/w).

Item 8. The composition of any of the preceding Items, wherein the composition comprises rosemary extract, ginger extract, and luteolin, and wherein the ratio between said rosemary extract, ginger extract, and luteolin is approximately 10:5:1 (w/w).

Item 9. The composition of any of the preceding Items, wherein the composition comprises rosemary extract, ashwagandha extract, and luteolin, the ratio between said rosemary extract, ashwagandha extract, and luteolin being approximately 30:10:4 (w/w).

Item 10. The composition of any of the preceding Items, wherein the composition comprises rosemary extract, ginger extract, luteolin and milk thistle extract, the ratio between said rosemary extract, ginger extract, luteolin and milk thistle extract being approximately 10:5:1:30 (w/w).

Item 11. The composition of any of the preceding Items, wherein the composition comprises rosemary extract, ginger extract, luteolin, milk thistle extract, and *Bacopa monnieri* extract, the ratio between said rosemary extract, ginger extract, luteolin, milk thistle extract and *Bacopa monnieri* extract being approximately 10:5:1:30:48 (w/w).

Item 12. The composition of any of the preceding Items, wherein the composition comprises rosemary extract, ginger extract, luteolin, and *Bacopa monnieri* extract, the ratio between said rosemary extract, ginger extract, luteolin, and *Bacopa monnieri* extract being approximately 10:5:1:48 (w/w).

Item 13. The composition of any of the preceding Items, wherein the composition is used to prevent and/or treat a disease or a condition selected from the group consisting of oxidative stress, detoxification, inflammation, cancer, or a related disease or condition.

Item 14. The composition of any of the preceding Items, wherein the composition is used as a nutritional supplement.

Item 15. The composition of any of the preceding Items, wherein the composition is in the form of a tablet, a capsule, a soft gel, a liquid, a lotion, a gel, a powder, an ointment, or an aerosol.

Item 16. A method of treating and/or preventing a disease or condition, comprising the step of administering a composition to a mammal, the composition comprising one or more phytochemicals selected from the group consisting of carnosol, carnosic acid, shogaol, gingerol, luteolin, and withaferin A, said one or more phytochemicals being present in the composition in an amount effective to activate the Nrf2 (NF-E2 related factor 2) pathway.

Item 17. The method of any of the preceding Items, wherein the composition comprises rosemary extract, ashwagandha extract, and luteolin, wherein the rosemary extract is specified at 5-10% carnosol, the ashwagandha extract is specified at 1-3% withaferin A, and the luteolin is specified at 95-99% luteolin, the ratio between said rosemary extract, ashwagandha extract, and luteolin being approximately 30:10:4 (w/w).

Item 18. The method of Item 17, wherein the composition comprises rosemary extract, ginger extract, and luteolin, wherein the rosemary extract is specified at 5-10% carnosol, the ginger extract is specified at 10-20% 6-shogaol, and the luteolin is specified at 95-99% luteolin, the ratio between said rosemary extract, ginger extract, and luteolin being approximately 10:5:1 (w/w).

Item 19. The method of any of Items 17-18, wherein the composition is administered orally to a human at 10-1000 mg per day.

Item 20. The method of any of Items 17-19, wherein the composition comprises at least two phytochemicals selected from the group consisting of carnosol, carnosic acid, shogaol, gingerol, luteolin, and withaferin A, wherein the at least two phytochemicals exert their effects on at least two different control points of the Nrf2 activation pathway, said control points being selected from the group consisting of control points A, B, C, D and E.

It will be readily apparent to those skilled in the art that the compositions and methods described herein may be modified and substitutions may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1 Effects on Nrf2 Action Pathways

Figure 4:
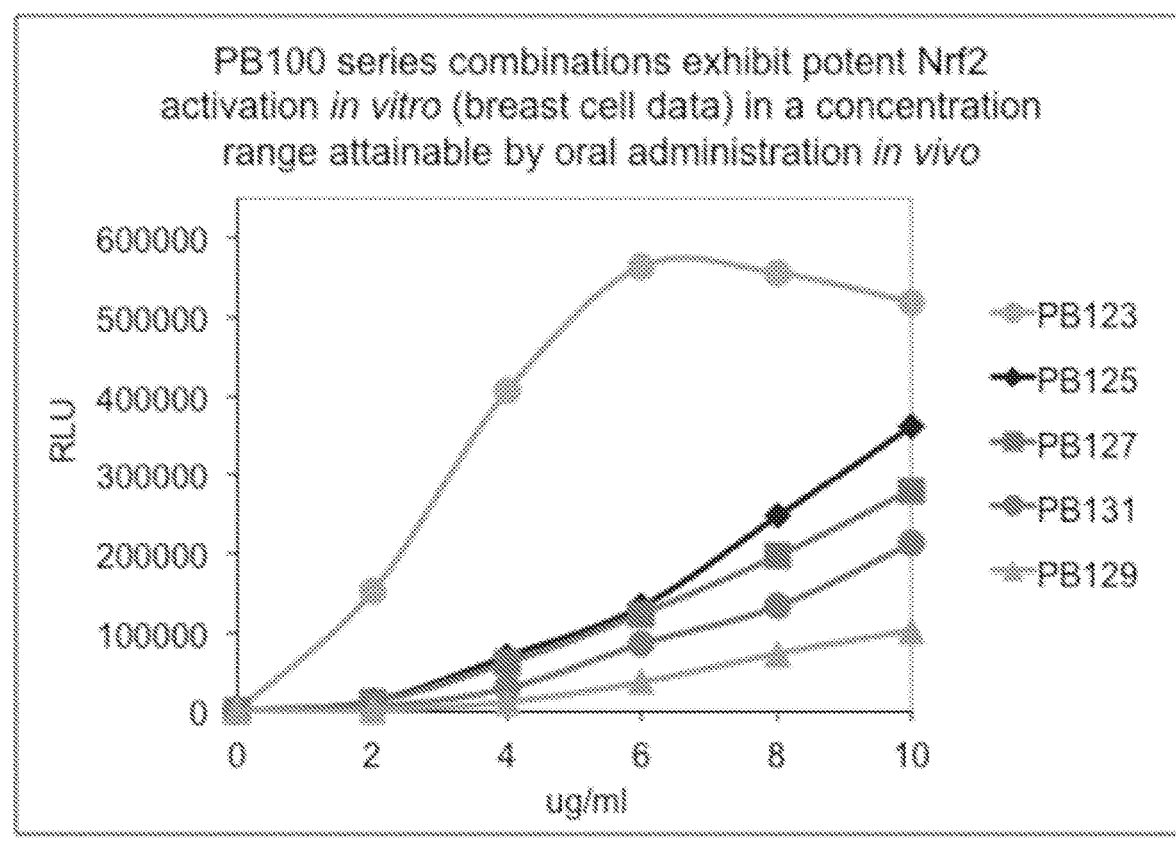
FIG. 4 shows Nrf2 activation induced by PB123, PB125, PB127, PB129, and PB131 in a transfected breast cancer cell line.
Figure 5:
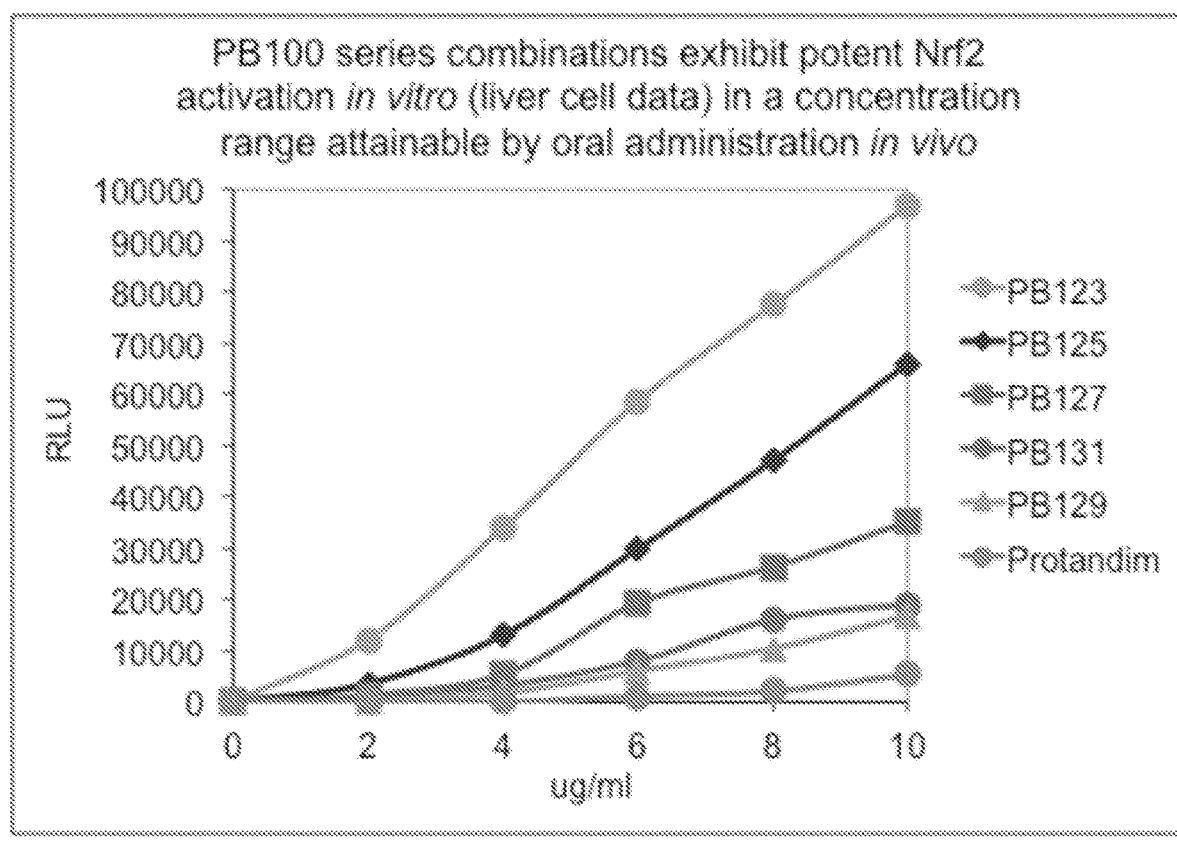
FIG. 5 shows Nrf2 activation induced by PB123, PB125, PB127, PB129, and PB131 in a transfected liver cancer cell line.

The different agents, PB123, PB125, PB127, PB129, and PB131, each exhibit strong, potent Nrf2 activation as demonstrated in vitro by using these combinations to treat cell lines that have been stably transfected with a promoter/reporter construct containing a known Nrf2-binding antioxidant response element inserted in to drive production of the readily detectable luciferase gene such that Nrf2 activation results in luciferase production which is detected by luciferin-dependent chemiluminescence. As shown in the FIGS. 4 and 5, potent Nrf2 activation is induced by the PB123, PB125, PB127, PB129, and PB131 combinations in transfected cancer cell lines independent of tissue type (breast and liver cell data are shown).

These control points include, but are not limited to, Control point A: release of Nrf2 from binding and inhibition by Keap1; Control point B: action on Nrf2 by enzymes such as kinases that phosphorylate and activate Nrf2; Control point C: activation of other transcription factors that improve the gene expression profile; Control point D: action on mechanisms such as Fyn that control the export of Nrf2 from the nucleus; and Control point E: degradation of Keap1 and mTOR inhibition by SESN2/SQSTM1/ULK1. See FIG. 1. For example the PB125 combination that includes rosemary (carnosol), ashwagandha (withaferin A), and luteolin acts at multiple control points in the Nrf2 activation pathway. In HepG2 cells stably transfected with an ARE-driven luciferase reporter gene we inhibited Fyn (with 5 µg/ml saracatinib; AZD0530, a Src family kinase inhibitor (Kaufman, Salazar et al. 2015)) and showed that the inhibition of Fyn increased Nrf2 activation caused by another dietary supplement Nrf2 activator (Protandim) by up to 9-fold. In contrast Fyn inhibition did not further increase PB125-induced Nrf2 activation, confirming that while other dietary Nrf2 activators such as Protandim allow the "shutdown pathway" to remain active, PB125 appears to block the pathway, permitting Nrf2 activation by a smaller amount of the PB125 dietary supplement combination.

Figure 6A:
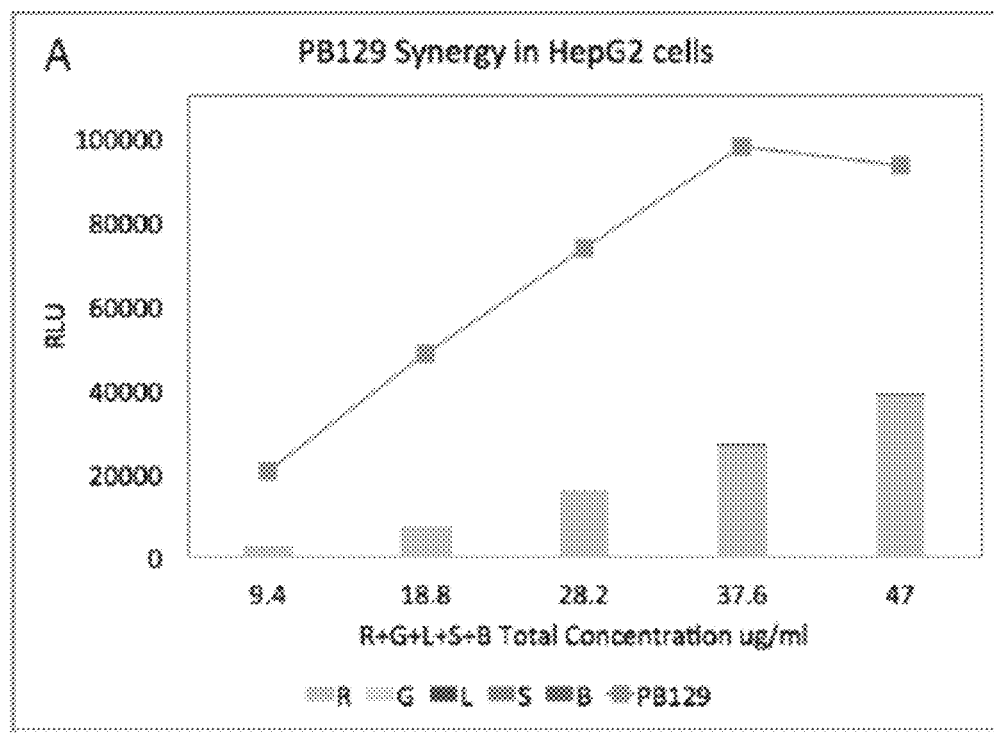
FIG. 6A-6C shows the synergistic effect of Nrf2 activation induced by PB129 in HepG2 (human liver, FIG. 6A), MCF7 (human breast, FIG. 6B), and A172 (human brain, FIG. 6C) cancer cell lines.
Figure 6B:
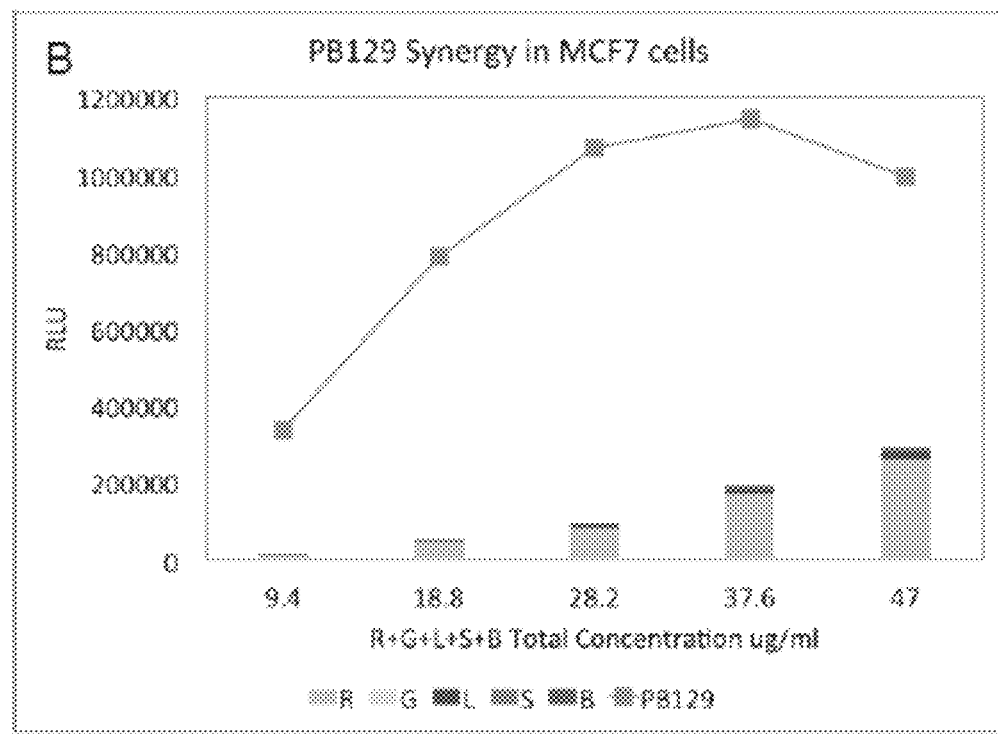
Figure 6C:
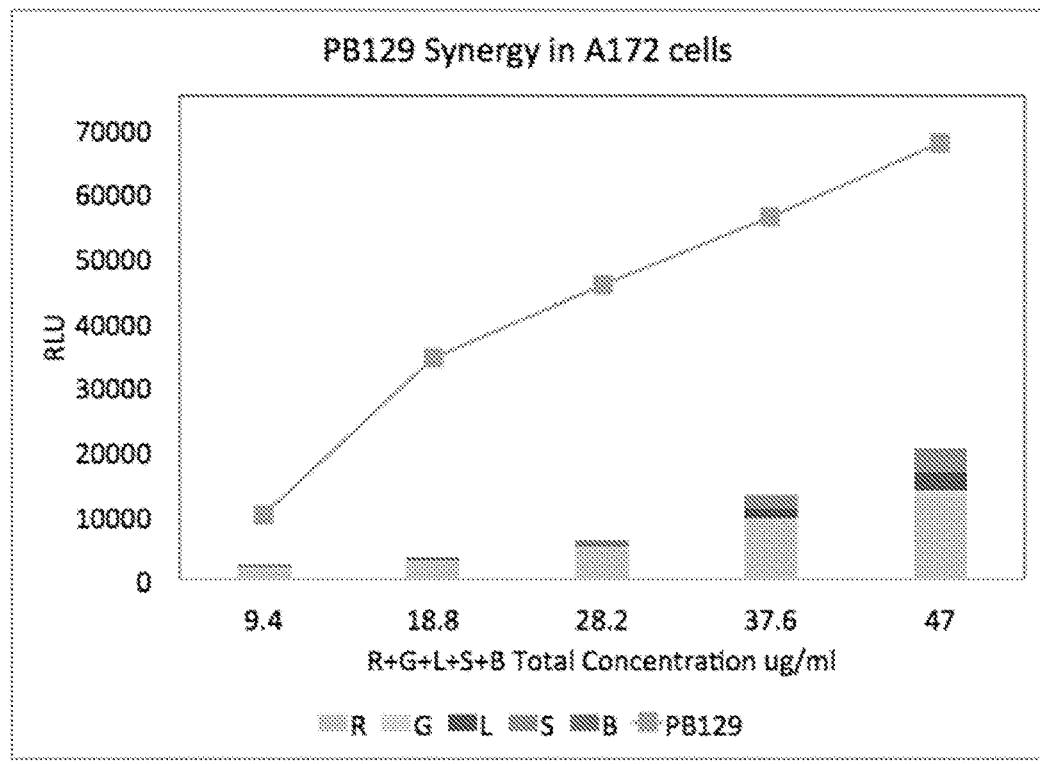
Figure 7A:
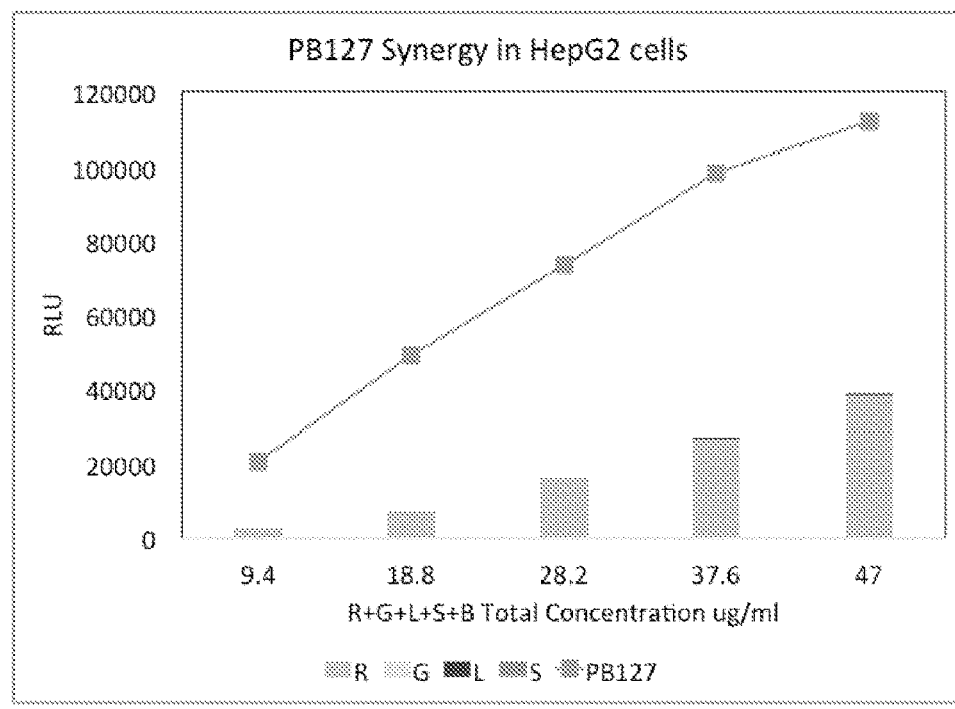
FIG. 7A-7C shows the synergistic effect of Nrf2 activation induced by PB127 in HepG2 (human liver, FIG. 7A), MCF7 (human breast, FIG. 7B), and A172 (human brain, FIG. 7C) cancer cell lines.
Figure 7B:
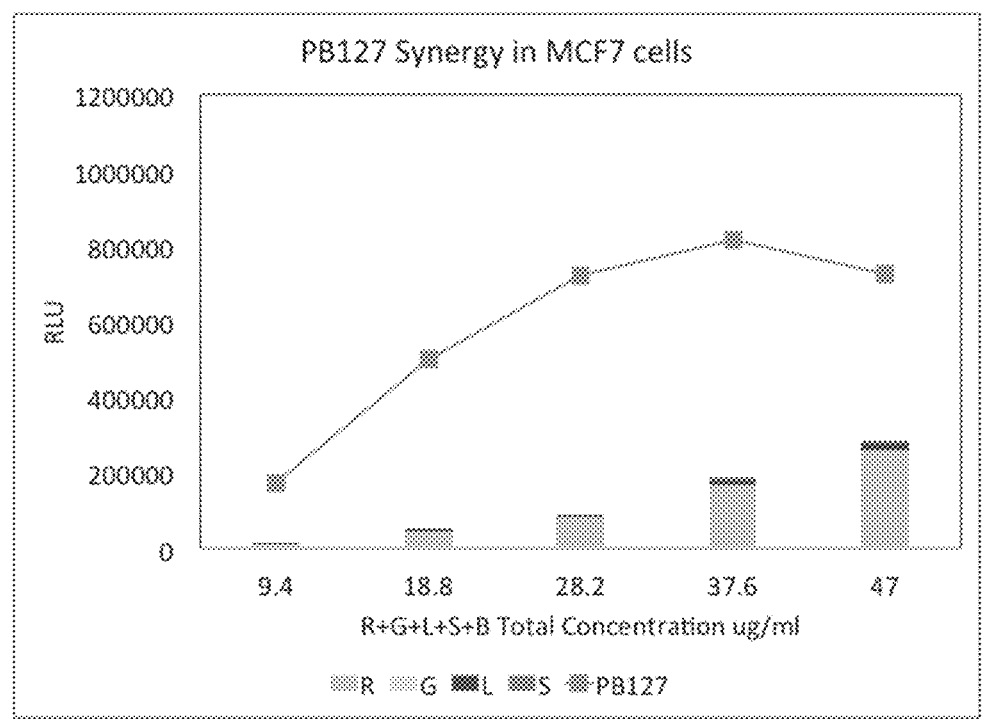
Figure 7C:
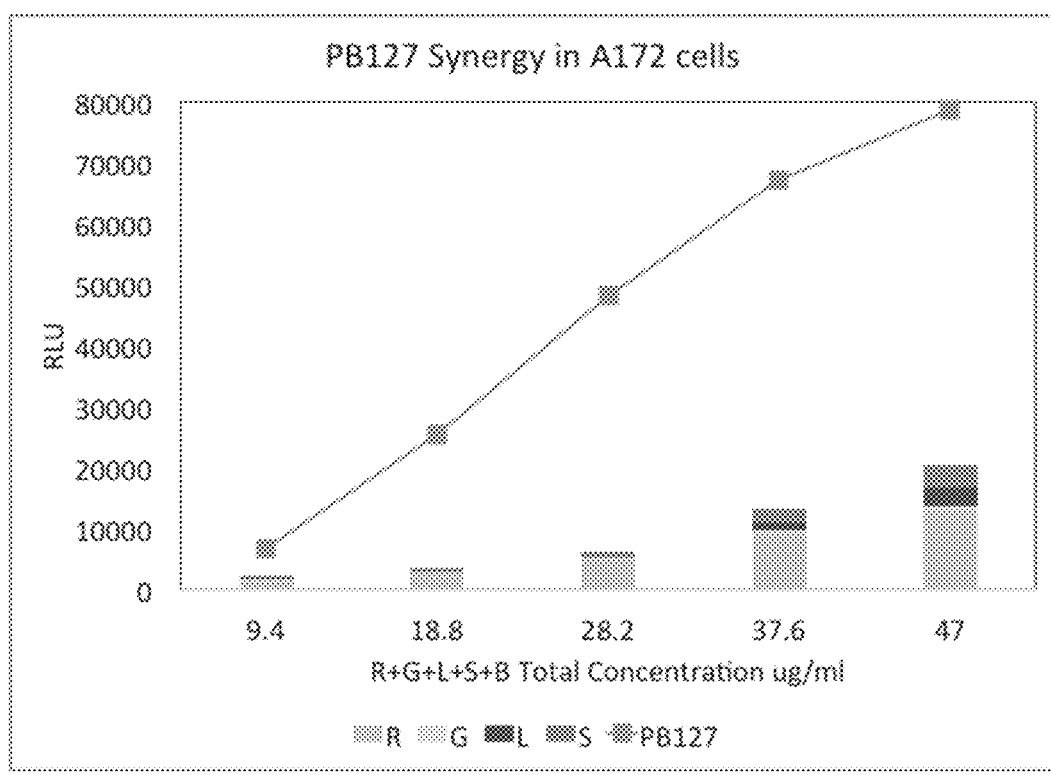

By acting on more than one of the control points, a combination of agents such as PB123 or PB125, along with related combinations based on the core Nrf2 activator triads in PB123 or PB125, such as PB127, PB129, or PB131 give an improved Nrf2 activation and gene regulation response and do so at lower doses than would be predicted based on known properties of the active agents in the combinations and based on what is taught by the prior art. The active ingredients in PB123, 125, PB127, PB129, and PB131 act together in a synergistic fashion, whereby the amount of Nrf2 activation and Nrf2-dependent gene expression is higher for the combined ingredients than would be predicted based on the sum of their individual activities on Nrf2 at the same concentrations, even in different cell types (FIGS. 6 and 7). One of the surprising findings was that relatively small amounts of luteolin added to the other ingredients gave a larger than expected increase in Nrf2 activation and gene regulation.

A rosemary (6.7% carnosol), ashwagandha (1% withaferin A), and luteolin (98% luteolin) combination of PB125 (at 30:10:4 rosemary:ashwagandha:luteolin) increased Nrf2-dependent gene expression in mice fed 35 days of PB125 added to mouse chow. See FIGS. 8 and 9.

Figure 8:
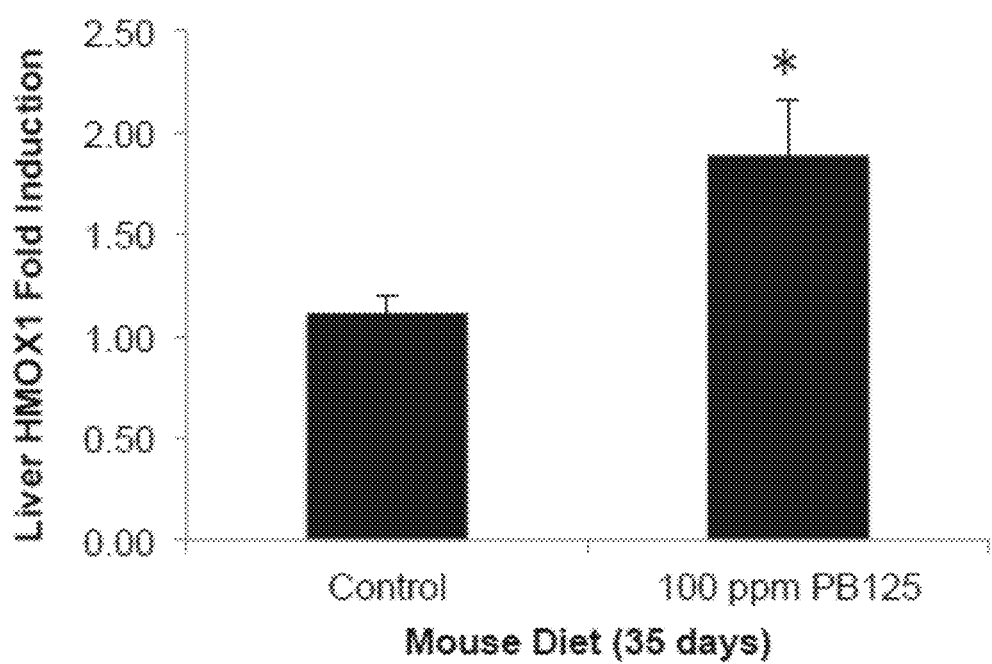
FIG. 8 shows increase of Mouse Liver HMOX1 gene expression in vivo.
Figure 9:
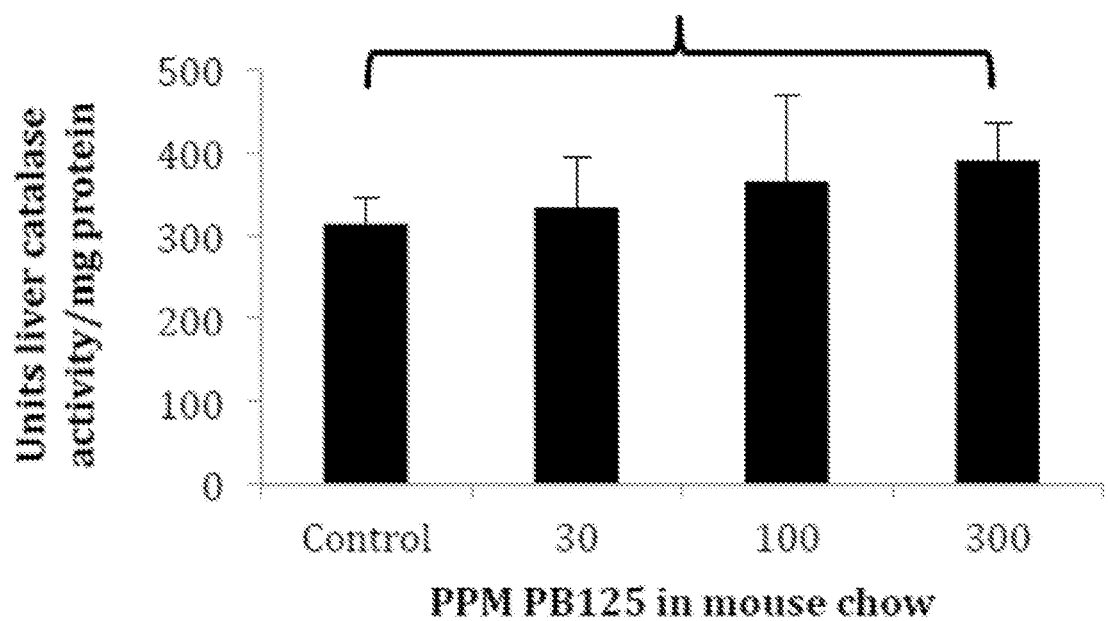
FIG. 9 shows Liver Catalase Activity Induced by PB125 in diet.

The PB125 phytochemical components are standardized, with rosemary extract (specified at 6% carnosol), ashwagandha extract (specified at 1% withaferin A), and luteolin (specified at 98% purity), so 100 ppm equates to $6.83 \times 10^{-5}$ mg rosemary extract, $2.27 \times 10^{-5}$ mg ashwagandha extract, and $9.43 \times 10^{-6}$ mg luteolin per g of diet. PB125 in mouse diet activates the Nrf2 pathway (e.g., increased hmox1 gene expression in mouse liver) and increases catalase activity. The PB125 dosages were well tolerated by mice as evidenced by no change compared to control diet in weight stability, consistent food intake, and no noticeable GI distress or changes in behavior. The 100 ppm PB125 diet produced significant increases in liver hmox1 gene expression in mice (measured after 35 days of diet consumption) (FIG. 8).

The individual ingredients in PB125, PB127, and PB129 have a long history of human consumption and proven safety in both humans and in animal studies (Sailer, Meier et al. 2001, Roodenrys, Booth et al. 2002, Aggarwal, Takada et al. 2004, Boon and Wong 2004, Anadon, Martinez-Larranaga et al. 2008, Zick, Djuric et al. 2008, Johnson 2011, Chandrasekhar, Kapoor et al. 2012, Theoharides, Asadi et al. 2012, Taliou, Zintzaras et al. 2013, Zhang, Gan et al. 2013, Gonzalez-Vallinas, Reglero et al. 2015, Kumar, Srivastava et al. 2015, Nabavi, Braidy et al. 2015, Petiwala and Johnson 2015). Rosemary, ashwagandha, ginger, milk thistle, Bacopa monnieri, and luteolin have been extensively studied in various diseases and have an extensive record of safe use (Mishra, Singh et al. 2000, Roodenrys, Booth et al. 2002, Aggarwal, Takada et al. 2004, Boon and Wong 2004). Rosemary (Rosmarinus officinalis) is a common Mediterranean herb widely consumed in foods as a spice and flavoring agent. Also, rosemary has a long history of use in traditional therapies for the treatment of a variety of disorders [1], with emphasis on anti-inflammatory (Emami, Ali-Beig et al. 2013), antioxidant (Klancnik, Guzej et al. 2009, Raskovic, Milanovic et al. 2014, Ortuno, Serrano et al. 2015), and antimicrobial benefits (Del Campo, Amiot et al. 2000, Bozin, Mimica-Dukic et al. 2007). Ashwagandha (Withania somnifera, also known as Indian winter cherry or Indian ginseng) is a member of the Solanaceae family of flowering plants. It has been utilized for centuries in South Asia in traditional therapies, with historical and current emphasis on immunomodulatory (Khan, Subramaneyaan et al. 2015), anti-tumor (Rai, Jogee et al. 2016), neurological (Raghavan and Shah 2015), anti-inflammatory (Kumar, Srivastava et al. 2015), antioxidant (Priyandoko, Ishii et al. 2011), and other benefits (Wankhede, Langade et al. 2015). Ginger has a long history of safe usage for pain, GI, and aging-related conditions, with evidence of benefit against oxidative stress (Wang, Zhang et al. 2014, Lakhan, Ford et al. 2015, Wilson 2015). Silymarin has a good safety profile (Saller, Meier et al. 2001, Jacobs, Dennehy et al. 2002) even in those with cirrhosis, and even at high doses (up to 900 mg a day) that are much higher than used in PB127 or PB129. Bacopa moniera has proven to be safe in human studies of memory loss at doses higher than used in PB129, and animal studies have not demonstrated any adverse toxicities for any of its components (Mishra, Singh et al. 2000, Roodenrys, Booth et al. 2002). Luteolin is a bioflavanoid flavone compound commonly consumed in the human diet from multiple food sources (e.g., onions, tea, apples, broccoli, olives, celery, spinach, oranges, oregano, etc.), resulting in a typical dietary intake of approximate 1 mg/day from normal from food sources (Chun, Chung et al. 2007, Seelinger, Merfort et al. 2008, Jun, Shin et al. 2015, Kim, Park et al. 2015, Nabavi, Braidy et al. 2015). Luteolin is frequently utilized as a dietary supplement with emphasis on its antioxidant (Sun, Sun et al. 2012), neurological (Xu, Wang et al. 2014), and anti-inflammatory benefits (Seelinger, Merfort et al. 2008, Taliou, Zintzaras et al. 2013, Paredes-Gonzalez, Fuentes et al. 2015).

Figure 10:
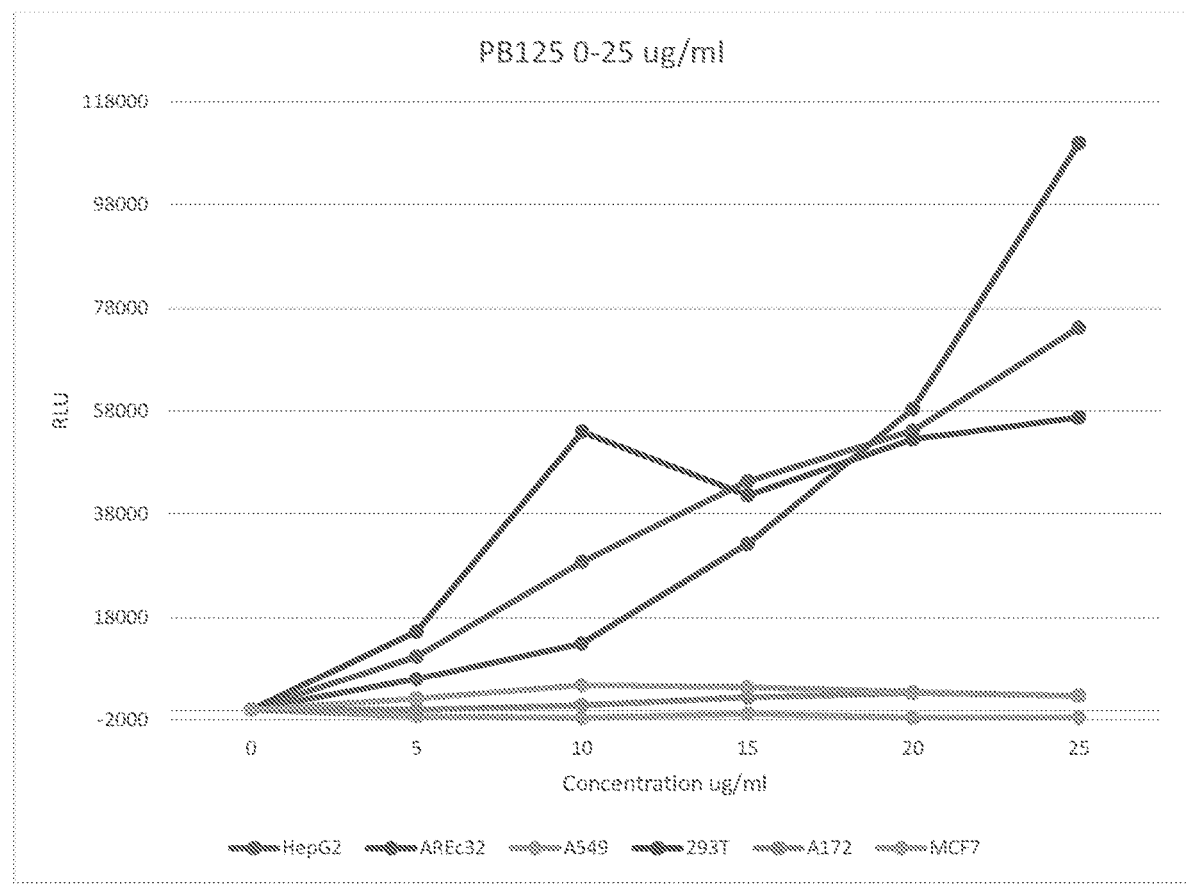
FIG. 10 shows overlay of relative light units (RLU) observed with added luciferin after ARE-driven luciferase gene expression was induced by treatment with PB125 in stably transfected HepG2 (human liver), AREc32 (human breast), MCF7 (human breast), A549 (human lung), 293T (human kidney), and A172 (human brain) cancer cell lines. Strong Nrf2 activation was observed in liver, kidney, and breast cell lines by 5, 10, 15, 20, and 25 micrograms of PB125 per mL of culture solution.

As an example of properties of PB125, we cultured cell lines that had been stably transfected with constructs of the luciferase gene driven in its promoter region by copies of the ARE Nrf2-binding sequence, known as promoter-reporter constructs (Simmons, Fan et al. 2011, Shukla, Huang et al. 2012). Briefly, the stably transfected cells of types HepG2 (human liver), AREc32 (human breast), MCF7 (human breast), A549 (human lung), 293T (human kidney), and A172 (human brain) were seeded at low density in 24-well plates and incubated at 37° C. with 10% CO2. After 24 h various concentrations of PB125 were added to the cells. After an additional 18 h of incubation, the cells were lysed in their wells with 100 µl of a lysing buffer that contains 3.5 mM sodium pyrophosphate to stabilize light output by luciferase. A 20 µl aliquot of cell lysate was added to a small test tube, placed in a BD Monolight 3010 luminometer for background luminescence, and then 50 µl of 1 mM luciferin was injected into the tube. Relative Light Units integrated for 10 sec were measured for each sample. The liver, breast, brain, and kidney cell types tested exhibited Nrf2 gene activation and luciferase expression by treatment with PB100-series combinations with (FIG. 10).

As an example of the cell protective mechanisms induced by PB125 treatment, we examined the gene upregulation in cells treated with PB125. Briefly, cultured HepG2 liver cells were treated with PB125 at 8 micrograms/mL concentration for 18 hours, then total RNA was extracted from the HepG2 cells by using the RNeasy Total RNA Isolation Kit (QIAGEN Inc. Valencia, Calif., USA). The concentration of each sample was determined based on the absorbance at 260 nm (A260). The purity of each sample was determined based on the ratio of A260 to A280. A range of 1.9-2.1 was considered adequately pure. The integrity of Total RNA samples was verified by Agilent 2200 Tape Station. Total RNA (250 ng) was converted to double-stranded cDNA (ds-cDNA) by using the cDNA synthesis kit (Affymetrix). An oligo-dT primer containing a T7 RNA polymerase promoter was utilized. The ds-cDNA was then purified and recovered by using purification beads (Affymetrix). Next, in vitro transcription was performed to generate biotin-labeled cRNA using a RNA Transcript Labeling Kit (Affymetrix). Biotin-labeled cRNA was purified using an RNeasy affinity column (Qiagen). To ensure optimal hybridization to the oligonucleotide array, the cRNA was fragmented. Fragmentation was performed such that the cRNA fragments are between 50-200 bases in length by incubating the cRNA at 94° C. for 35 mM in a fragmentation buffer. The sample was then added to a hybridization solution containing 100 mM MES, 1 M Na+, and 20 mM EDTA in the presence of 0.01% Tween 20. The final concentration of the fragmented cRNA was 0.05 µg/µL. Hybridization was performed by incubating 200 uL of the sample to the Affymetrix GeneChip® PrimeView™ human gene expression array (Affymetrix Inc., Santa Clara, Calif., USA) at 45° C. for 16 hours using a GeneChip® Hybridization Oven 640 (Affymetrix). After hybridization, the hybridization solutions were removed and the arrays were washed and stained with Streptavidin-phycoerythrin using a GeneChip® Fluidics Station 450 (Affymetrix). Arrays were read at a resolution of 2.5 to 3 microns using the GeneChip Scanner 3000 (Affymetrix). Each gene was represented by the use of ~11 probes per transcript and many control probes. The Command Console GeneChip software program was used to determine the intensity of expression for all genes on the array. For this experiment, fold-induction of genes by PB125 treatment of HepG2 cells was calculated compared to the average intensity observed in control HepG2 cells in culture solution without any added stimulus such as PB125. As depicted in Table 1, genes upregulated by PB125 included a variety of Nrf2-regulated antioxidant, anti-inflammatory, cell stress response and other protective genes. These genes include, for example, genes involved in GSH production and regeneration, iron sequestration, GSH utilization, thioredoxin (TXN) production, regeneration and ultilization, etc. Table 1 lists relevant example genes that are upregulated by PB125. In summary, this example supports that the mechanism of cellular protection by PB125 involves activation of the Nrf2 cell signaling pathway.

TABLE 1

Gene Microarray analysis revealed that PB125 regulates numerous Nrf2 associated genes and genes associated with antioxidant, anti-inflammatory, and other cell protective effects.

| Probe Set ID | HepG2 (Control) | Fold Induction by BP125 | Representative Public ID | Gene Title | Gene Symbol |
|---|---|---|---|---|---|
| 11715650_a_at | 45.53 | 10.10 | AF208018.1 | thioredoxin reductase 1 | TXNRD1 |
| 11756634_a_at | 414.69 | 2.81 | CR597200.1 | glutathione reductase | GSR |
| 11750770_a_at | 1005.93 | 2.37 | AK304288.1 | glutamate-cysteine ligase, catalytic subunit | GCLC |
| 11759710_at | 199.19 | 2.04 | BC024223.2 | thioredoxin domain containing 9 | TXNDC9 |
| 11744680_a_at | 231.18 | 7.72 | AB040875.1 | solute carrier family 7 (anionic amino acid transporter light chain, xc-system), member 11 | SLC7A11 |
| 11756634_a_at | 414.69 | 2.81 | CR597200.1 | glutathione reductase | GSR |
| 11716939_a_at | 1217.99 | 8.63 | NM_002133.1 | heme oxygenase (decycling) 1 | HMOX1 |
| 11725496_a_at | 488.83 | 8.87 | NM_032717.3 | 1-acylglycerol-3-phosphate O-acyltransferase 9 | AGPAT9 |
| 11752577_at | 771.67 | 3.62 | AY258285.1 | ferritin, heavy polypeptide 1 | FTH1 |
| 11715649_s_at | 3236.76 | 4.73 | NM_003330.2 | thioredoxin reductase 1 | TXNRD1 |
| 11716950_s_at | 1908.04 | 5.45 | NM_080725.1 | sulfiredoxin 1 | SRXN1 |
| 11752843_x_at | 1202.52 | 4.54 | AK304877.1 | sequestosome 1 | SQSTM1 |
| 11750416_a_at | 69.07 | 9.41 | AK293322.1 | thioredoxin reductase 1 | TXNRD1 |
| 11756585_a_at | 86.47 | 6.47 | CR614710.1 | aquaporin 3 (Gill blood group) | AQP3 |
| 11735676_a_at | 231.82 | 3.98 | NM_182980.2 | oxidative stress induced growth inhibitor 1 | OSGIN1 |
| 11753445_a_at | 244.58 | 10.37 | BT019785.1 | heme oxygenase (decycling) 1 | HMOX1 |
| 11723490_at | 1195.87 | 6.07 | BC041809.1 | glutamate-cysteine ligase, modifier subunit | GCLM |
| 11756915_a_at | 63.77 | 8.33 | AL833940.1 | cytochrome P450, family 4, subfamily F, polypeptide 11 | CYP4F11 |
| 11736655_a_at | 499.98 | 7.20 | NM_012212.3 | prostaglandin reductase 1 | PTGR1 |
| 11719171_a_at | 2722.97 | 6.99 | NM_001353.5 | aldo-keto reductase family 1, member C1 (dihydrodiol dehydrogenase 1; 20-alpha (3-alpha)-hydroxysteroid dehydrogenase) | AKR1C1 |
| 11742378_a_at | 1112.08 | 4.32 | NM_001080538.1 | aldo-keto reductase family 1, member B10 (aldose reductase) /// aldo-keto reductase family 1, member B15 | AKR1B10 /// AKR1B15 |
| 11729101_a_at | 2435.26 | 6.95 | NM_205845.1 | aldo-keto reductase family 1, member C2 (dihydrodiol dehydrogenase 2; bile acid binding protein; 3-alpha hydroxysteroid dehydrogenase, type III) /// aldo-keto reductase family 1 member C2-like | AKR1C2 /// LOC100653286 |

TABLE 1-continued

Gene Microarray analysis revealed that PB125 regulates numerous Nrf2 associated genes and genes associated with antioxidant, anti-inflammatory, and other cell protective effects.

| Probe Set ID | HepG2 (Control) | Fold Induction by BP125 | Representative Public ID | Gene Title | Gene Symbol |
|---|---|---|---|---|---|
| 11757882_x_at | 59.22 | 2.02 | BU784580 | glutathione S-transferase alpha 1 /// glutathione S-transferase alpha 2 | GSTA1 /// GSTA2 |

Figure 11:
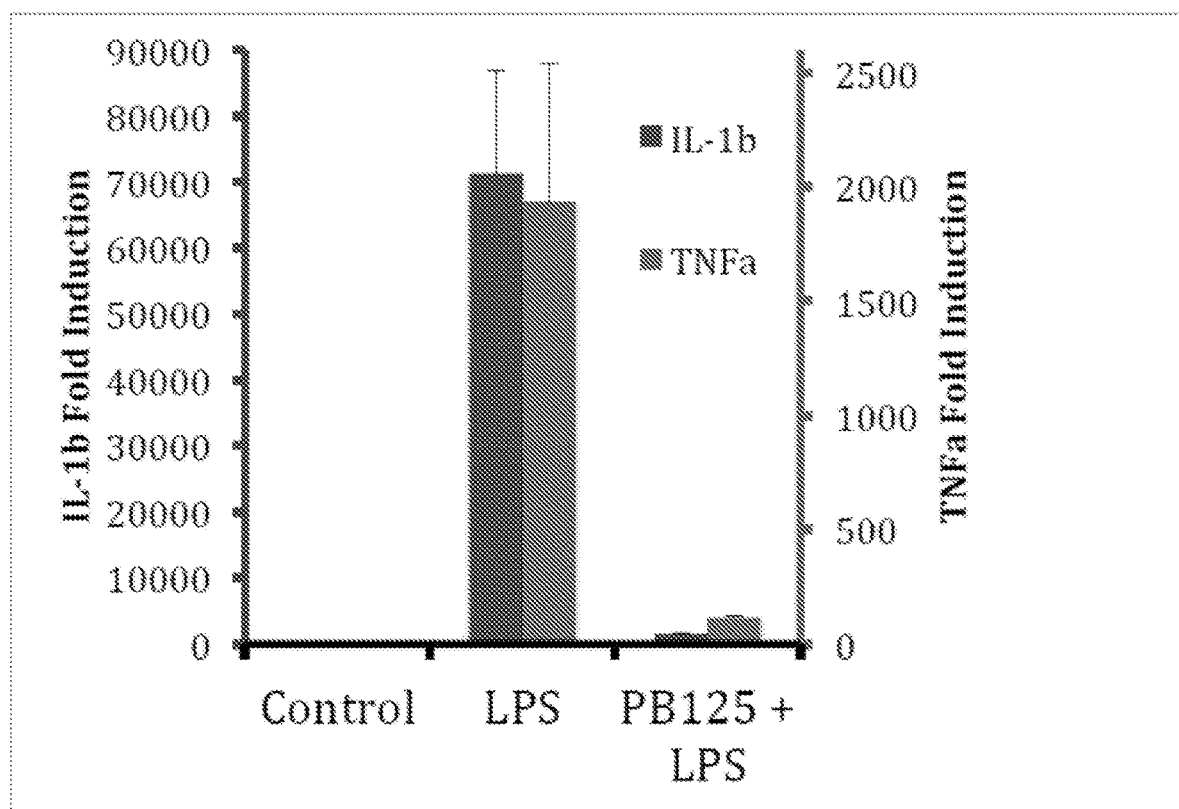
FIG. 11 shows that PB125 decreases LPS-induced expression of inflammatory genes.

As an example of the anti-inflammatory mechanisms induced by PB125 treatment, we examined cytokine levels in primary cells treated with PB125 and stimulated with bacterial lipopolysaccharide endotoxin (LPS). Mouse peritoneal macrophages were obtained after treatment with thioglycollate into the peritoneal cavity for 1 week followed by lavage recovery of approximately 7 million macrophages. Aliquots of cells were plated and treated with ethanol control (0.1% to match PB125) or PB125 (5 ug/mL) for 16 h, then stimulated with lipopolysaccharide (100 ng/mL) or vehicle (negative control) for 5 h. Total RNA was isolated from the cells for quantitative PCR analysis to measure TNFα (tumor necrosis factor-alpha) and IL-1β (interleukin-1 beta) gene expression, normalized to 18s levels. Notably, PB125 treatment caused a dramatic decrease in LPS-induced expression of the pro-inflammatory cytokines TNFα and IL-1β. See FIG. 11.

Figure 13:
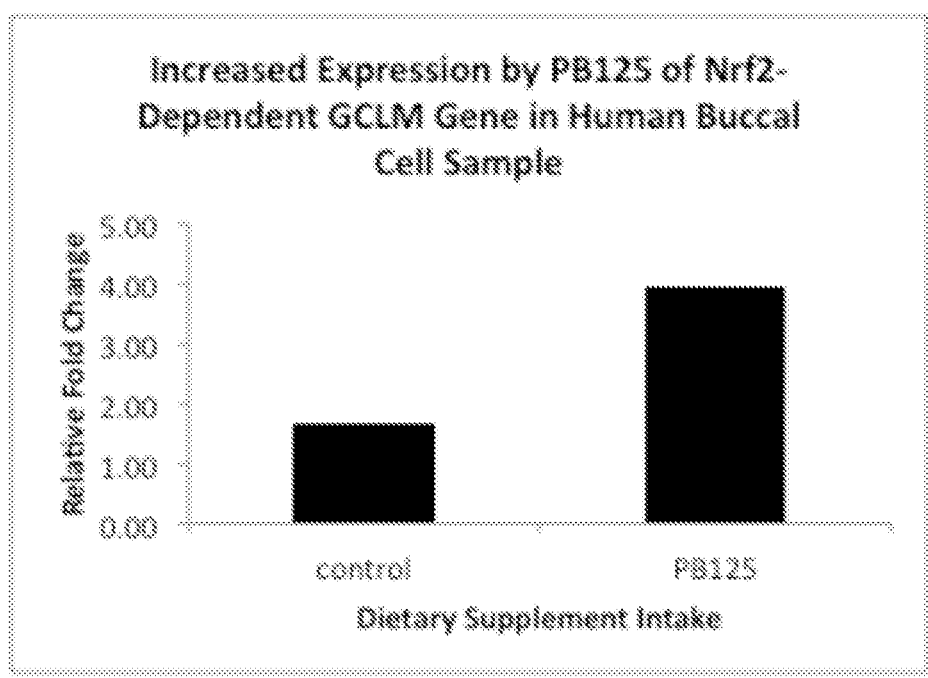
FIG. 13 shows higher GCLM gene expression as a result of PB125 administration.

A rosemary (6.7% carnosol), ashwagandha (1% withaferin A), and luteolin (98% luteolin) combination of PB125 (at 30:10:4 rosemary:ashwagandha:luteolin) increased Nrf2-dependent gene expression of the GCLM gene in buccal cell samples from a human subject taking 60 mg of PB125 daily p.o., compare to buccal cell samples two normal control subjects (assayed by quantitative RT-PCR on purified RNA, using human GCLM specific primers (Forward Primer: TTGCCTCCTGCTGTGTGATG (SEQ ID NO. 1), Reverse Primer: GTGCGCTTGAATGTCAGGAA) (SEQ ID NO. 2), normalized to GAPDH, with relative fold change calculated by the 2^(delta delta Ct) method. See FIG. 13.

As additional data supporting the invention, we found surprising amounts of synergy between the Rosemary, Ginger, Ashwagandha, and Luteolin ingredients. For example, low concentrations of Luteolin synergized with combinations of Rosemary extracts and Ginger extracts to activate Nrf2. In the present invention, other agents can be added to the Nrf2-activating combinations provided they do not interfere with the Nrf2 activating functionality. We found that the silymarin and bacosides ingredients did not antagonize the Nrf2 activation of the Rosemary, Ginger, Ashwagandha, and Luteolin ingredients.

Following up on this experiment in another way, luciferase RLU measured 17, 24, 41, and 48 hours after treatment of HepG2 cells in which the PB125 treatment at 0-10 ug/mL and 0-50 ug/mL ranges was washed off after 2 hours of exposure time and replaced by fresh cell culture media showed that Nrf2-driven production of luciferase was highest at 17 h, then rapidly decreased to approximately baseline levels by 48 hours after treatment.

Repeating treatments on cultured HepG2 cells with 2 hour exposures once every 24 hours, then read 24 hours later showed that the Nrf2 activation by PB125 wore off between 24 and 48 hours and the cells could still be activated again if treated again with PB125.

Figure 12:
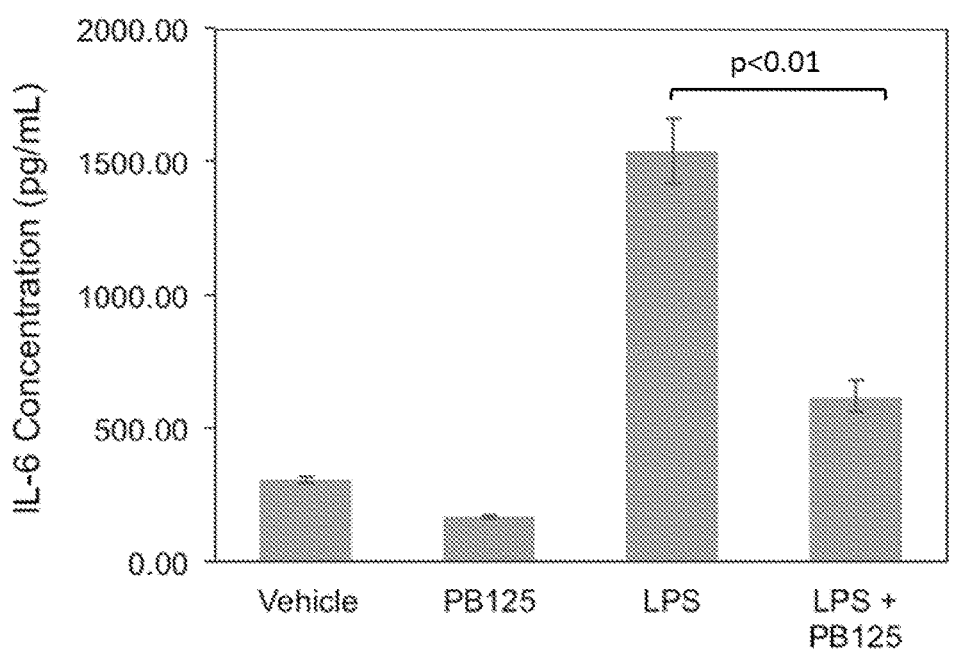
FIG. 12 shows that PB125 decreases LPS-induced expression of IL-6.

As an example of the anti-inflammatory mechanisms induced by PB123 or PB125 treatment, we examined gene expression and cytokine levels in primary human pulmonary artery endothelial cells (HPAEC) treated with PB123 or PB125 and stimulated with bacterial lipopolysaccharide endotoxin (LPS). LPS stimulation induced the expression of inflammation-related genes, and this upregulation was attenuated by treatment with PB123 or PB125. Table 2 shows the 40 genes most highly upregulated by LPS treatment, and shows that both PB123 treatment and PB125 treatment attenuated LPS-induced gene expression. LPS stimulation increased the release of pro-inflammatory interleukin-6 (IL6) protein from the HPAEC cells, and this increase was attenuated by treatment with PB125. See FIG. 12.

TABLE 2

Gene Microarray analysis revealed that PB123 and PB125 exhibited anti-inflammatory effects. Both PB123 and PB125 lowered the LPS-induced expression signals of the 40 genes that were the most highly up-regulated by LPS.

| Gene Symbol | Control | LPS | LPS + PB123 | LPS + PB125 | Gene Title | Gene Symbol | LPS/LPS + PB123 | LPS/LPS + PB125 |
|---|---|---|---|---|---|---|---|---|
| CXCL3 | 33 | 1441 | 492 | 225 | chemokine (C-X-C motif) ligand 3 | CXCL3 | 2.9 | 6.4 |
| CCL20 | 196 | 4776 | 2055 | 1034 | chemokine (C-C motif) ligand 20 | CCL20 | 2.3 | 4.6 |
| CXCL2 | 292 | 5407 | 2956 | 2669 | chemokine (C-X-C motif) ligand 2 | CXCL2 | 1.8 | 2.0 |
| C5F2 | 41 | 621 | 132 | 133 | colony stimulating factor 2 (granulocyte-macrophage) | CSF2 | 4.7 | 4.7 |
| TNFAIP6 | 33 | 390 | 91 | 60 | tumor necrosis factor, alpha-induced protein 6 | TNFAIP6 | 4.3 | 6.5 |
| IL8 | 590 | 6750 | 5571 | 4257 | Interleukin 8 | IL8 | 1.2 | 1.6 |
| TNFAIP2 | 285 | 3089 | 798 | 512 | tumor necrosis factor, alpha-induced protein 2 | TNFAIP2 | 3.9 | 6.0 |
| CXCL10 | 67 | 668 | 47 | 31 | chemokine (C-X-C motif) ligand 10 | CXCL10 | 14.3 | 21.3 |
| CXCL1 | 1195 | 11398 | 7858 | 7819 | chemokine (C-X-C motif) ligand 1 (melanoma growth stimulating activity, alpha) | CXCL1 | 1.5 | 1.5 |

TABLE 2-continued

Gene Microarray analysis revealed that PB123 and PB125 exhibited anti-inflammatory effects. Both PB123 and PB125 lowered the LPS-induced expression signals of the 40 genes that were the most highly up-regulated by LPS.

| Gene Symbol | Control | LPS | LPS + PB123 | LPS + PB125 | Gene Title | Gene Symbol | LPS/LPS + PB123 | LPS/LPS + PB125 |
|---|---|---|---|---|---|---|---|---|
| CX3CL1 | 386 | 3618 | 444 | 288 | chemokine (C-X3-C motif) ligand 1 | CX3CL1 | 8.2 | 12.5 |
| BIRC3 | 86 | 798 | 349 | 190 | baculoviral IAP repeat containing 3 | BIRC3 | 2.3 | 4.2 |
| CD69 | 36 | 333 | 111 | 45 | CD69 molecule | CD69 | 3.0 | 7.3 |
| TNFAIP3 | 94 | 814 | 309 | 190 | tumor necrosis factor, alpha-induced protein 3 | TNFAIP3 | 2.6 | 4.3 |
| SELE | 1465 | 12425 | 5605 | 2612 | selectin E | SELE | 2.2 | 4.8 |
| CXCL6 | 245 | 1683 | 458 | 178 | chemokine (C-X-C motif) ligand 6 (granulocyte chemotactic protein 2) | CXCL6 | 3.7 | 9.5 |
| NKX3-1 | 60 | 398 | 141 | 125 | NK3 homeobox 1 | NKX3-1 | 2.8 | 3.2 |
| CSF3 | 92 | 592 | 272 | 290 | colony stimulating factor 3 (granulocyte) | C5F3 | 2.2 | 2.0 |
| RND1 | 98 | 601 | 224 | 236 | Rho family GTPase 1 | RND1 | 2.7 | 2.5 |
| LTB | 244 | 1478 | 374 | 314 | lymphotoxin beta (TNF superfamily, member 3) | LTB | 3.9 | 4.7 |
| FAM101A /// ZNF664 | 63 | 329 | 70 | 78 | family with sequence similarity 101, member A /// protein FAM101A | FAM101A /// ZNF664 | 4.7 | 4.2 |
| CXCL5 | 163 | 844 | 127 | 63 | chemokine (C-X-C motif) ligand 5 | CXCL5 | 6.7 | 13.3 |
| CEBPD | 183 | 947 | 493 | 489 | CCAAT/enhancer binding protein (C/EBP), delta | CEBPD | 1.9 | 1.9 |
| MAP3K8 | 26 | 128 | 75 | 45 | mitogen-activated protein kinase kinase kinase 8 | MAP3K8 | 1.7 | 2.9 |
| TRAF1 | 158 | 730 | 421 | 328 | TNF receptor-associated factor 1 | TRAF1 | 1.7 | 2.2 |
| IL6 | 429 | 1967 | 1166 | 1105 | interleukin 6 (interferon, beta 2) | IL6 | 1.7 | 1.8 |
| VCAM1 | 1315 | 5963 | 2065 | 1116 | vascular cell adhesion molecule 1 | VCAM1 | 2.9 | 5.3 |
| ICAM1 | 288 | 1290 | 543 | 416 | Intercellular adhesion molecule 1 | ICAM1 | 2.4 | 3.1 |
| SLC7A2 | 356 | 1592 | 660 | 383 | solute carrier family 7 (cationic amino acid transporter, y+ system), member 2 | SLC7A2 | 2.4 | 4.2 |
| CXCR7 | 291 | 1286 | 660 | 521 | chemokine (C-X-C motif) receptor 7 | CXCR7 | 1.9 | 2.5 |
| NCOA7 | 132 | 561 | 212 | 137 | nuclear receptor coactivator 7 | NCOA7 | 2.6 | 4.1 |
| IRF1 | 240 | 1014 | 579 | 489 | interferon regulatory factor 1 | IRF1 | 1.8 | 2.1 |
| BCL2A1 | 31 | 130 | 39 | 18 | BCL2-related protein A1 | BCL2A1 | 3.3 | 7.0 |
| TNFRSF9 | 32 | 124 | 33 | 30 | tumor necrosis factor receptor superfamily, member 9 | TNFRSF9 | 3.7 | 4.1 |
| IL1A | 236 | 888 | 589 | 561 | interleukin 1, alpha | IL1A | 1.5 | 1.6 |
| MT1G | 36 | 134 | 116 | 163 | metallothionein 1G | MT1G | 1.2 | 0.8 |
| TIFA | 81 | 293 | 175 | 147 | TRAF-interacting protein with forkhead-associated domain | TIFA | 1.7 | 2.0 |
| CCL5 | 95 | 330 | 95 | 83 | chemokine (C-C motif) ligand 5 | CCL5 | 3.5 | 4.0 |
| CAB39 | 26 | 91 | 48 | 43 | calcium binding protein 39 | CAB39 | 1.9 | 2.1 |
| SOC51 | 29 | 95 | 73 | 76 | suppressor of cytokine signaling 1 | SOCS1 | 1.3 | 1.2 |
| IL1B | 52 | 170 | 58 | 66 | interleukin 1, beta | IL1B | 2.9 | 2.6 |

Example 2 PB125

One embodiment of the present disclosure is a combination of rosemary extract (specified at 5 to 50% carnosol), ashwagandha extract (specified at 0.5-10% withaferin A), and luteolin (specified at 10-100% luteolin), in the mass ratios of 30:10:6, 30:10:5, 30:10:4, or 30:10:1 with a daily human dose of the combination ranging from 42 to 1050 mg as shown in Table 3.

TABLE 3

Composition with specifications for the ingredients and the daily dose ranges of PB125 for human

| | Ingredient: | | |
|---|---|---|---|
| | Rosemary | Ashwagandha | Luteolin |
| Spec range: | 5-50% carnosol or 10-100% diterpenes | 0.5-10% withaferin A | 10-100% luteolin |
| Preferred spec range: | 5-10% carnosol | 1-3% withaferin A | 95-99% luteolin |
| Daily dose range: | 30-750 mg | 10-250 mg | 2-50 mg |
| Composition range: | 30-90% | 10-30% | 2-8% |
| Preferred mass ratio | 30 | 10 | 6 |
| Preferred mass ratio | 30 | 10 | 5 |
| Preferred mass ratio | 30 | 10 | 4 |
| Preferred mass ratio | 30 | 10 | 1 |

Example 3 PB127

Another embodiment of the present disclosure is a PB127 combination of rosemary extract (specified at 5 to 10% carnosol), ginger extract (specified at 1-10% 6-shogaol and/or 10-25% 6-gingerol), luteolin (specified at 90-100% luteolin), and milk thistle extract (specified at 50-90% silymarin), in the mass ratio of 10:5:1:30, respectively, with a daily human dose of the combination ranging from 46 to 920 mg as shown in Table 4.

TABLE 4

Composition with specifications for the ingredients and the daily dose ranges of PB127 for human

|  | Ingredient: | | | |
| --- | --- | --- | --- | --- |
|  | Rosemary | Ginger | Luteolin | Milk Thistle |
| Spec range: | 5-50% carnosol or 10-100% diterpenes | 0.5-20% 6-shogaol or 6-gingerol | 10-100% luteolin | 10-100% silymarin |
| Preferred spec range: | 5-10% carnosol | 10-20% 6-shogaol | 95-99% luteolin | 75-100% silymarin |
| Daily dose range: | 10-200 mg | 5-100 mg | 1-20 mg | 30-600 mg |
| Composition range: | 10-30% | 5-15% | 1-3% | 25-75% |
| Preferred mass ratio | 10 | 5 | 1 | 30 |

Example 4 PB129

Another embodiment of the present disclosure is a PB129 combination of rosemary extract (specified at 5 to 10% carnosol), ginger extract (specified at 1-10% 6-shogaol and/or 10-25% 6-gingerol), luteolin (specified at 90-100% luteolin), milk thistle extract (specified at 50-90% silymarin), and *Bacopa monnieri* extract (specified at 10-60% bacosides) in the mass ratio of 10:5:1:30:48, respectively, with a daily human dose of the combination ranging from 94 to 1820 mg as shown in Table 5.

TABLE 5

Composition with specifications for the ingredients and the daily dose ranges of PB129 for human

|  | Ingredient: | | | | |
| --- | --- | --- | --- | --- | --- |
|  | Rosemary | Ginger | Luteolin | Milk Thistle | Bacopa |
| Spec range: | 5-50% carnosol or 10-100% diterpenes | 0.5-20% 6-shogaol or 6-gingerol | 10-100% luteolin | 10-100% silymarin | 10-80% bacosides |
| Preferred spec range: | 5-10% carnosol | 10-20% 6-shogaol | 95-99% luteolin | 75-100% silymarin | 20-60% bacosides |
| Daily dose range: | 10-200 mg | 5-100 mg | 1-20 mg | 30-600 mg | 48-900 mg |
| Composition range: | 5-15% | 2.5-7.5% | 0.5-1.5% | 12.5-37.5% | 25-75% |
| Preferred mass ratio | 10 | 5 | 1 | 30 | 48 |

Example 5 PB123

Another embodiment of the present disclosure is a PB123 combination of rosemary extract (specified at 5 to 10% carnosol), ginger extract (specified at 1-10% 6-shogaol and/or 10-25% 6-gingerol), luteolin (specified at 90-100% luteolin) in the mass ratio of 10:5:1, respectively, with a daily human dose of the combination ranging from 16 to 320 mg as shown in Table 6.

TABLE 6

Composition with specifications for the ingredients and the daily dose ranges of PB123 for human

|  | Ingredient: | | |
| --- | --- | --- | --- |
|  | Rosemary | Ginger | Luteolin |
| Spec range: | 5-50% carnosol or 10-100% diterpenes | 0.5-20% 6-shogaol or 6-gingerol | 10-100% luteolin |
| Preferred spec range: | 5-10% carnosol | 10-20% 6-shogaol | 95-99% luteolin |
| Daily dose range: | 10-200 mg | 5-100 mg | 1-20 mg |
| Composition range: | 10-30% | 5-15% | 1-3% |
| Preferred mass ratio | 10 | 5 | 1 |

Example 6 PB131

Another embodiment of the present invention is a PB131 combination of rosemary extract (specified at 5 to 10% carnosol), ginger extract (specified at 1-10% 6-shogaol and/or 10-25% 6-gingerol), luteolin (specified at 90-100% luteolin) and *Bacopa monnieri* extract (specified at 10-60% bacosides) in the mass ratio of 10:5:1:48, respectively, with a daily human dose of the combination ranging from 64 to 1220 mg as shown in Table 7.

TABLE 7

Composition with specifications for the ingredients and the daily dose ranges of PB131 for human

|  | Ingredient: | | | |
| --- | --- | --- | --- | --- |
|  | Rosemary | Ginger | Luteolin | Bacopa |
| Spec range: | 5-50% carnosol or 10-100% diterpenes | 0.5-20% 6-shogaol or 6-gingerol | 10-100% luteolin | 10-80% bacosides |
| Preferred spec range: | 5-10% carnosol | 10-20% 6-shogaol | 95-99% luteolin | 20-60% bacosides |
| Daily dose range: | 10-200 mg | 5-100 mg | 1-20 mg | 48-900 mg |
| Composition range: | 5-15% | 2.5-7.5% | 0.5-1.5% | 25-75% |
| Preferred mass ratio | 10 | 5 | 1 | 48 |

The contents of all cited references (including literature references, patents, patent applications, and websites) that may be cited throughout this application or listed below are hereby expressly incorporated by reference in their entirety for any purpose into the present disclosure. The disclosure may employ, unless otherwise indicated, conventional techniques of microbiology, molecular biology and cell biology, which are well known in the art.

The disclosed methods and systems may be modified without departing from the scope hereof. It should be noted that the matter contained in the above description or shown in the accompanying drawings should be interpreted as illustrative and not in a limiting sense.

LIST OF REFERENCES

The following references, patents and publication of patent applications are either cited in this disclosure or are of relevance to the present disclosure. All documents listed below, along with other papers, patents and publication of patent applications cited throughout this disclosures, are hereby incorporated by reference as if the full contents are reproduced herein.

Aggarwal, B. B., Y. Takada and O. V. Oommen (2004). "From chemoprevention to chemotherapy: common targets and common goals." Expert Opin Investig Drugs 13(10): 1327-1338.

Anadon, A., M. R. Martinez-Larranaga, M. A. Martinez, I. Ares, M. R. Garcia-Risco, F. J. Senorans and G. Reglero (2008). "Acute oral safety study of rosemary extracts in rats." J Food Prot 71(4): 790-795.

Baitharu, I., V. Jain, S. N. Deep, S. Shroff, J. K. Sahu, P. K. Naik and G. Ilavazhagan (2014). "Withanolide A prevents neurodegeneration by modulating hippocampal glutathione biosynthesis during hypoxia." PLoS One 9(10): e105311.

Bjelakovic, G., D. Nikolova, L. L. Gluud, R. G. Simonetti and C. Gluud (2007). "Mortality in randomized trials of antioxidant supplements for primary and secondary prevention: systematic review and meta-analysis." JAMA 297(8): 842-857.

Bocci, V. and G. Valacchi (2015). "Nrf2 activation as target to implement therapeutic treatments." Front Chem 3: 4.

Boon, H. and J. Wong (2004). "Botanical medicine and cancer: a review of the safety and efficacy." Expert Opin Pharmacother 5(12): 2485-2501.

Boutten, A., D. Goven, J. Boczkowski and M. Bonay (2010). "Oxidative stress targets in pulmonary emphysema: focus on the Nrf2 pathway." Expert Opin Ther Targets 14(3): 329-346.

Bozin, B., N. Mimica-Dukic, I. Samojlik and E. Jovin (2007). "Antimicrobial and antioxidant properties of rosemary and sage (Rosmarinus officinalis L. and Salvia officinalis L, Lamiaceae) essential oils." J Agric Food Chem 55(19): 7879-7885.

Chandrasekhar, K., J. Kapoor and S. Anishetty (2012). "A prospective, randomized double-blind, placebo-controlled study of safety and efficacy of a high-concentration full-spectrum extract of ashwagandha root in reducing stress and anxiety in adults." Indian J Psychol Med 34(3): 255-262.

Cho, H. Y. and S. R. Kleeberger (2010). "Nrf2 protects against airway disorders." Toxicol Appl Pharmacol 244 (1): 43-56.

Chun, O. K., S. J. Chung and W. O. Song (2007). "Estimated dietary flavonoid intake and major food sources of U.S. adults." J Nutr 137(5): 1244-1252.

Del Campo, J., M. J. Amiot and C. Nguyen—The (2000). "Antimicrobial effect of rosemary extracts." J Food Prot 63(10): 1359-1368.

Eggler, A. L., K. A. Gay and A. D. Mesecar (2008). "Molecular mechanisms of natural products in chemoprevention: induction of cytoprotective enzymes by Nrf2." Mol Nutr Food Res 52 Suppl 1: S84-94.

Emami, F., H. Ali-Beig, S. Farahbakhsh, N. Mojabi, B. Rastegar-Moghadam, S. Arbabian, M. Kazemi, E. Tekieh, L. Golmanesh, M. Ranjbaran, C. Jalili, A. Noroozzadeh and H. Sahraei (2013). "Hydroalcoholic extract of Rosemary (Rosmarinus officinalis L.) and its constituent carnosol inhibit formalin-induced pain and inflammation in mice." Pak J Biol Sci 16(7): 309-316.

Gonzalez-Vallinas, M., G. Reglero and A Ramirez de Molina (2015). "Rosemary (Rosmarinus officinalis L.) Extract as a Potential Complementary Agent in Anticancer Therapy." Nutr Cancer: 1-9.

Heistad, D. D., Y. Wakisaka, J. Miller, Y. Chu and R. Pena-Silva (2009). "Novel aspects of oxidative stress in cardiovascular diseases." Circ J 73(2): 201-207.

Huang, Y., W. Li, Z.-y. Su and A.-N. T. Kong (2015). "The complexity of the Nrf2 pathway: Beyond the antioxidant response." The Journal of Nutritional Biochemistry: in press.

Hybertson, B. M. and B. Gao (2014). "Role of the Nrf2 signaling system in health and disease." Clin Genet 86(5): 447-452.

Jacobs, B. P., C. Dennehy, G Ramirez, J. Sapp and V. A. Lawrence (2002). "Milk thistle for the treatment of liver disease: a systematic review and meta-analysis." Am J Med 113(6): 506-515.

Johnson, D. A. and J. A. Johnson (2015). "Nrf2-a therapeutic target for the treatment of neurodegenerative diseases." Free Radic Biol Med.

Johnson, J. J. (2011). "Carnosol: A promising anti-cancer and anti-inflammatory agent." Cancer letters 305(1): 1-7.

Jun, S., S. Shin and H. Joung (2015). "Estimation of dietary flavonoid intake and major food sources of Korean adults." Br J Nutr: 1-10.

Kaufman, A. C., S. V. Salazar, L. T. Haas, J. Yang, M. A. Kostylev, A. T. Jeng, S. A. Robinson, E. C. Gunther, C. H. van Dyck, H. B. Nygaard and S. M. Strittmatter (2015). "Fyn inhibition rescues established memory and synapse loss in Alzheimer mice." Ann Neurol 77(6): 953-971.

Kensler, T. W., N. Wakabayashi, S. L. Slocum, J. J. Skoko and S. Shin (2010). "When Nrf2 Talks, Who's Listening?" Antioxid Redox Signal.

Khan, M. A., M. Subramaneyaan, V. K. Arora, B. D. Banerjee and R. S. Ahmed (2015). "Effect of Withania somnifera (Ashwagandha) root extract on amelioration of oxidative stress and autoantibodies production in collagen-induced arthritic rats." J Complement Integr Med 12(2): 117-125.

Kim, Y. J., M. Y. Park, N. Chang and O. Kwon (2015). "Intake and major sources of dietary flavonoid in Korean adults: Korean National Health and Nutrition Examination Survey 2010-2012." Asia Pac J Clin Nutr 24(3): 456-463.

Klancnik, A., B. Guzej, M. H. Kolar, H. Abramovic and S. S. Mozina (2009). "In vitro antimicrobial and antioxidant activity of commercial rosemary extract formulations." J Food Prot 72(8): 1744-1752.

Koehn, F. E. (2006). "Therapeutic potential of natural product signal transduction agents." Curr Opin Biotechnol 17(6): 631-637.

Koehn, F. E. and G. T. Carter (2005). "The evolving role of natural products in drug discovery." Nat Rev Drug Discov 4(3): 206-220.

Kumar, G., A. Srivastava, S. K. Sharma, T. D. Rao and Y. K. Gupta (2015). "Efficacy & safety evaluation of Ayurvedic treatment (Ashwagandha powder & Sidh Makardhwaj) in rheumatoid arthritis patients: a pilot prospective study." Indian J Med Res 141(1): 100-106.

Kyung-Soo, C., K. Juthika, C. In Gyeong and K. and Joydeb Kumar (2014). "Carnosol: A Phenolic Diterpene With Cancer Chemopreventive Potential." Journal of Cancer Prevention 19(2): 103-110.

Lakhan, S. E., C. T. Ford and D. Tepper (2015). "Zingiberaceae extracts for pain: a systematic review and meta-analysis." Nutr J 14: 50.

Lee, K. H. (2010). "Discovery and development of natural product-derived chemotherapeutic agents based on a medicinal chemistry approach." J Nat Prod 73(3): 500-516.

Maher, J. and M. Yamamoto (2010). "The rise of antioxidant signaling—the evolution and hormetic actions of Nrf2." Toxicol Appl Pharmacol 244(1): 4-15.

Martin, D., A. I. Rojo, M. Salinas, R. Diaz, G. Gallardo, J. Alam, C. M. R. de Galarreta and A. Cuadrado (2004). "Regulation of Heme Oxygenase-1 Expression through the Phosphatidylinositol 3-Kinase/Akt Pathway and the Nrf2 Transcription Factor in Response to the Antioxidant Phytochemical Carnosol." Journal of Biological Chemistry 279(10): 8919-8929.

Mishra, L. C., B. B. Singh and S. Dagenais (2000). "Scientific basis for the therapeutic use of Withania somnifera (ashwagandha): a review." Altern Med Rev 5(4): 334-346.

Moon, E. J. and A. Giaccia (2015). "Dual roles of NRF2 in tumor prevention and progression: possible implications in cancer treatment." Free Radic Biol Med 79: 292-299.

Nabavi, S. F., N. Braidy, O. Gortzi, E. Sobarzo-Sanchez, M. Daglia, K. Skalicka-Woźniak and S. M. Nabavi (2015). "Luteolin as an anti-inflammatory and neuroprotective agent: A brief review." Brain Research Bulletin 119, Part A: 1-11.

Ortuno, J., R. Serrano and S. Banon (2015). "Antioxidant and antimicrobial effects of dietary supplementation with rosemary diterpenes (carnosic acid and carnosol) vs vitamin E on lamb meat packed under protective atmosphere." Meat Sci 110: 62-69.

Paredes-Gonzalez, X., F. Fuentes, S. Jeffery, C. L. Saw, L. Shu, Z. Y. Su and A. T. Kong (2015). "Induction of NRF2-mediated gene expression by dietary phytochemical flavones apigenin and luteolin." Biopharm Drug Dispos.

Pechanova, O. and F. Simko (2009). "Chronic antioxidant therapy fails to ameliorate hypertension: potential mechanisms behind." J Hypertens 27 Suppl 6: S32-36.

Petiwala, S. M. and J. J. Johnson (2015). "Diterpenes from rosemary (Rosmarinus officinalis): Defining their potential for anti-cancer activity." Cancer Lett 367(2): 93-102.

Priyandoko, D., T. Ishii, S. C. Kaul and R. Wadhwa (2011). "Ashwagandha leaf derived withanone protects normal human cells against the toxicity of methoxyacetic acid, a major industrial metabolite." PLoS One 6(5): e19552.

Raghavan, A. and Z. A. Shah (2015). "Withania somnifera: a pre-clinical study on neuroregenerative therapy for stroke." Neural Regen Res 10(2): 183-185.

Rai, M., P. S. Jogee, G. Agarkar and C. A. Santos (2016). "Anticancer activities of Withania somnifera: Current research, formulations, and future perspectives." Pharm Biol 54(2): 189-197.

Raskovic, A., I. Milanovic, N. Pavlovic, T. Cebovic, S. Vukmirovic and M. Mikov (2014). "Antioxidant activity of rosemary (Rosmarinus officinalis L.) essential oil and its hepatoprotective potential." BMC Complement Altern Med 14: 225.

Roodenrys, S., D. Booth, S. Bulzomi, A. Phipps, C. Micallef and J. Smoker (2002). "Chronic effects of Brahmi (Bacopa monnieri) on human memory." Neuropsychopharmacology 27(2): 279-281.

Sailer, R., R. Meier and R. Brignoli (2001). "The use of silymarin in the treatment of liver diseases." Drugs 61(14): 2035-2063.

Saremi, A. and R. Arora (2009). "Vitamin E and Cardiovascular Disease." Am J Ther.

Satoh, H., T. Moriguchi, K. Taguchi, J. Takai, J. M. Maher, T. Suzuki, P. T. Winnard, Jr., V. Raman, M. Ebina, T. Nukiwa and M. Yamamoto (2010). "Nrf2-deficiency creates a responsive microenvironment for metastasis to the lung." Carcinogenesis 31(10): 1833-1843.

Satoh, T., K. Kosaka, K. Itoh, A. Kobayashi, M. Yamamoto, Y. Shimojo, C. Kitajima, J. Cui, J. Kamins, S. Okamoto, M. Izumi, T. Shirasawa and S. A. Lipton (2008). "Carnosic acid, a catechol-type electrophilic compound, protects neurons both in vitro and in vivo through activation of the Keap1/Nrf2 pathway via S-alkylation of targeted cysteines on Keap1." J Neurochem 104(4): 1116-1131.

Seelinger, G., I. Merfort and C. M. Schempp (2008). "Anti-oxidant, anti-inflammatory and anti-allergic activities of luteolin." Planta Med 74(14): 1667-1677.

Sekhar, K. R. and M. L. Freeman (2015). "NRF2 promotes survival following exposure to ionizing radiation." Free Radic Biol Med.

Shukla, S. J., R. Huang, S. O. Simmons, R. R. Tice, K. L. Witt, D. Vanleer, R. Ramabhadran, C. P. Austin and M. Xia (2012). "Profiling environmental chemicals for activity in the antioxidant response element signaling pathway using a high throughput screening approach." Environ Health Perspect 120(8): 1150-1156.

Simmons, S. O., C. Y. Fan, K. Yeoman, J. Wakefield and R. Ramabhadran (2011). "NRF2 Oxidative Stress Induced by Heavy Metals is Cell Type Dependent." Curr Chem Genomics 5: 1-12.

Sun, G. B., X. Sun, M. Wang, J. X. Ye, J. Y. Si, H. B. Xu, X. B. Meng, M. Qin, J. Sun, H. W. Wang and X. B. Sun (2012). "Oxidative stress suppression by luteolin-induced heme oxygenase-1 expression." Toxicol Appl Pharmacol 265(2): 229-240.

Suzuki, T. and M. Yamamoto (2015). "Molecular basis of the Keap1-Nrf2 system." Free Radic Biol Med.

Taliou, A., E. Zintzaras, L. Lykouras and K. Francis (2013). "An open-label pilot study of a formulation containing the anti-inflammatory flavonoid luteolin and its effects on behavior in children with autism spectrum disorders." Clin Ther 35(5): 592-602.

Theoharides, T. C., S. Asadi and S. Panagiotidou (2012). "A case series of a luteolin formulation (NeuroProtek®) in children with autism spectrum disorders." Int J Immunopathol Pharmacol 25(2): 317-323.

Vaishnavi, K., N. Saxena, N. Shah, R. Singh, K. Manjunath, M. Uthayakumar, S. P. Kanaujia, S. C. Kaul, K. Sekar and R. Wadhwa (2012). "Differential activities of the two closely related withanolides, Withaferin A and Withanone: bioinformatics and experimental evidences." PLoS One 7(9): e44419.

Velmurugan, K., J. Alam, J. M. McCord and S. Pugazhenthi (2009). "Synergistic induction of heme oxygenase-1 by the components of the antioxidant supplement Protandim." Free Radic Biol Med 46(3): 430-440.

Wang, S., C. Zhang, G. Yang and Y. Yang (2014). "Biological properties of 6-gingerol: a brief review." Nat Prod Commun 9(7): 1027-1030.

Wankhede, S., D. Langade, K. Joshi, S. R. Sinha and S. Bhattacharyya (2015). "Examining the effect of Withania somnifera supplementation on muscle strength and recovery: a randomized controlled trial." J Int Soc Sports Nutr 12: 43.

Wen, Z., Z. Wang, S. Wang, R. Ravula, L. Yang, J. Xu, C. Wang, Z. Zuo, M. S. Chow, L. Shi and Y. Huang (2011). "Discovery of molecular mechanisms of traditional Chinese medicinal formula Si-Wu-Tang using gene expression microarray and connectivity map." PLoS One 6(3): e18278.

Wilson, P. B. (2015). "Ginger (Zingiber officinale) as an Analgesic and Ergogenic Aid in Sport: A Systemic Review." J Strength Cond Res 29(10): 2980-2995.

Wu, P. S., J. H. Yen, M. C. Kou and M. J. Wu (2015). "Luteolin and Apigenin Attenuate 4-Hydroxy-2-Nonenal- Mediated Cell Death through Modulation of UPR, Nrf2-ARE and MAPK Pathways in PC12 Cells." PLoS One 10(6): e0130599.

Xiang, Q., Z. Liu, Y. Wang, H. Xiao, W. Wu, C. Xiao and X. Liu (2013). "Carnosic acid attenuates lipopolysaccharide-induced liver injury in rats via fortifying cellular antioxidant defense system." Food and Chemical Toxicology 53(0): 1-9.

Xu, J., H. Wang, K. Ding, L. Zhang, C. Wang, T. Li, W. Wei and X. Lu (2014). "Luteolin provides neuroprotection in models of traumatic brain injury via the Nrf2-ARE pathway." Free Radic Biol Med 71: 186-195.

Zhang, Y. C., F. F. Gan, S. B. Shelar, K. Y. Ng and E. H. Chew (2013). "Antioxidant and Nrf2 inducing activities of luteolin, a flavonoid constituent in Ixeris sonchifolia Hance, provide neuroprotective effects against ischemia-induced cellular injury." Food Chem Toxicol 59: 272-280.

Zick, S. M., Z. Djuric, M. T. Ruffin, A. J. Litzinger, D. P. Normolle, S. Alrawi, M. R. Feng and D. E. Brenner (2008). "Pharmacokinetics of 6-gingerol, 8-gingerol, 10-gingerol, and 6-shogaol and conjugate metabolites in healthy human subjects." Cancer Epidemiol Biomarkers Prev 17(8): 1930-1936.

What is claimed is:

1. A composition comprising rosemary extract, ginger extract, and luteolin, wherein the ratio between rosemary extract, ginger extract, and luteolin in the composition is approximately 10:5:1 (w/w), wherein said rosemary extract, ginger extract, and luteolin in said ratio synergistically activate Nrf2 (Nuclear-factor-erythroid 2 related factor 2) pathway in human cells when administered to the human cells.

2. The composition of claim 1, wherein the composition further comprises milk thistle extract, the ratio between said rosemary extract, ginger extract, luteolin and milk thistle extract being approximately 10:5:1:30 (w/w).

3. The composition of claim 2, wherein the composition further comprises *Bacopa monnieri* extract, the ratio between said rosemary extract, ginger extract, luteolin, milk thistle extract and *Bacopa monnieri* extract being approximately 10:5:1:30:48 (w/w).

4. The composition of claim 1, wherein the composition further comprises *Bacopa monnieri* extract, the ratio between said rosemary extract, ginger extract, luteolin, and *Bacopa monnieri* extract being approximately 10:5:1:48 (w/w).

5. The composition of claim 1, wherein the composition is in the form of a nutritional supplement.

6. The composition of claim 1, wherein the composition is in the form of a tablet, a capsule, a soft gel, a liquid, a lotion, a gel, a powder, an ointment, or an aerosol.

7. The composition of claim 1, wherein said rosemary extract is specified at 5-10% carnosol, said ginger extract is specified at 1-10% 6-shogaol, said luteolin is specified at 95-99% luteolin.

8. The composition of claim 1, wherein said rosemary extract is specified at 5-10% carnosol, said ginger extract is specified at 10-25% 6-gingerol, said luteolin is specified at 95-99% luteolin.

9. A composition comprising rosemary extract, ashwagandha extract, and luteolin, wherein the ratio between rosemary extract, ashwagandha extract, and luteolin in the composition is approximately 30:10:4 (w/w), wherein said rosemary extract, ashwagandha extract, and luteolin in said ratio synergistically activate Nrf2 (Nuclear-factor-erythroid 2 related factor 2) pathway in human cells when administered to the human cells.

10. The composition of claim 9, wherein said rosemary extract is specified at 5-10% carnosol, said ashwagandha extract is specified at 1-3% withaferin A, said luteolin is specified at 95-99% luteolin.

11. A method of treating a disease or condition in a subject comprising the step of administering the composition of claim 1 to the subject.

12. A method of treating a disease or condition in a subject comprising the step of administering the composition of claim 9 to the subject.

13. The method of claim 11, wherein the composition is administered orally to a human at 10-1000 mg per day.

14. The method of claim 12, wherein the composition is administered orally to a human at 10-1000 mg per day.

* * * * *